US008097254B2

(12) United States Patent
Neri et al.

(10) Patent No.: US 8,097,254 B2
(45) Date of Patent: Jan. 17, 2012

(54) SPECIFIC BINDING MOLECULES FOR SCINTIGRAPHY, CONJUGATES CONTAINING THEM AND THERAPEUTIC METHOD FOR TREATMENT OF ANGIOGENESIS

(75) Inventors: Dario Neri, Zürich (CH); Lorenzo Tarli, Monteriggioni (IT); Francesca Viti, Genoa (IT); Manfred Birchler, Zürich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 1357 days.

(21) Appl. No.: 10/821,930

(22) Filed: Apr. 12, 2004

(65) Prior Publication Data

US 2006/0133994 A1 Jun. 22, 2006

Related U.S. Application Data

(63) Continuation of application No. 09/512,082, filed on Feb. 24, 2000, now abandoned, which is a continuation-in-part of application No. 09/300,425, filed on Apr. 28, 1999, now abandoned, which is a continuation-in-part of application No. 09/075,338, filed on May 11, 1998, now abandoned.

(51) Int. Cl.
*A61K 39/00* (2006.01)
*A61K 39/395* (2006.01)
*A61K 51/00* (2006.01)
*A61K 38/39* (2006.01)
*C07K 14/515* (2006.01)

(52) U.S. Cl. ............... 424/142.1; 424/143.1; 424/1.11; 424/178.1; 514/9.3; 514/13.3

(58) Field of Classification Search .................. None
See application file for complete search history.

(56) References Cited

U.S. PATENT DOCUMENTS

| | | | |
|---|---|---|---|
| 4,341,223 A | 7/1982 | Lutz | |
| 4,741,900 A * | 5/1988 | Alvarez et al. | 424/1.53 |
| 4,894,326 A | 1/1990 | Matsuura et al. | |
| 5,120,830 A | 6/1992 | Santoro et al. | |
| 5,177,015 A | 1/1993 | Matsuura et al. | |
| 5,243,029 A | 9/1993 | Matusuura et al. | |
| 5,460,785 A * | 10/1995 | Rhodes et al. | 424/1.49 |
| 5,523,229 A | 6/1996 | Feinberg et al. | |
| 5,534,254 A | 7/1996 | Huston et al. | |
| 5,576,195 A | 11/1996 | Robinson et al. | |
| 5,583,203 A | 12/1996 | Hemler et al. | |
| RE35,500 E | 5/1997 | Rhodes | |
| 5,648,485 A | 7/1997 | Dolphin et al. | |
| 5,710,134 A | 1/1998 | Bosslet et al. | |
| 5,734,025 A | 3/1998 | Komai et al. | |
| 5,747,452 A | 5/1998 | Ruoslahti et al. | |
| 5,817,776 A | 10/1998 | Goodman et al. | |
| 5,831,088 A | 11/1998 | Dolphin et al. | |
| 5,837,813 A | 11/1998 | Ruoslahti et al. | |
| 5,843,156 A | 12/1998 | Slepian et al. | |
| 5,849,701 A | 12/1998 | Roberts et al. | |
| 5,876,691 A | 3/1999 | Chester et al. | |
| 5,877,289 A * | 3/1999 | Thorpe et al. | 530/387.1 |
| 5,913,884 A | 6/1999 | Trauner et al. | |
| 5,965,132 A * | 10/1999 | Thorpe et al. | 424/1.49 |
| 5,976,535 A | 11/1999 | Fritzberg et al. | |
| 5,997,842 A * | 12/1999 | Chen | 424/1.29 |
| 6,004,555 A * | 12/1999 | Thorpe et al. | 424/181.1 |
| 6,015,897 A | 1/2000 | Theodore et al. | |
| 6,036,955 A * | 3/2000 | Thorpe et al. | 424/136.1 |
| 6,051,230 A * | 4/2000 | Thorpe et al. | 424/178.1 |
| 6,083,485 A | 7/2000 | Licha et al. | |
| 6,093,399 A * | 7/2000 | Thorpe et al. | 424/182.1 |
| 6,121,426 A * | 9/2000 | Vogel et al. | 530/402 |
| 6,140,470 A | 10/2000 | Garen et al. | |
| 6,171,578 B1 | 1/2001 | Dean et al. | |
| 6,267,722 B1 | 7/2001 | Anderson et al. | |
| 6,296,831 B1 | 10/2001 | Weller et al. | |
| 6,342,219 B1 | 1/2002 | Thorpe et al. | |
| 6,342,326 B1 | 1/2002 | Milton | |
| 6,394,952 B1 | 5/2002 | Anderson et al. | |
| 6,630,570 B1 | 10/2003 | Licha et al. | |
| 6,696,245 B2 | 2/2004 | Winter et al. | |
| 6,749,853 B1 * | 6/2004 | Thorpe et al. | 424/182.1 |
| 7,125,541 B2 * | 10/2006 | Thorpe et al. | 424/1.49 |
| 7,129,254 B2 * | 10/2006 | Berger et al. | 514/340 |

(Continued)

FOREIGN PATENT DOCUMENTS

AU 779026 B2 1/2005

(Continued)

OTHER PUBLICATIONS

Neri et al, Advanced Drug Delivery Reviews, Apr. 6, 1998, vol. 31, 1998, pp. 43-52.*
Thorpe et al, Biophysical Journal, vol. 68, May 1995, pp. 2198-2206, Dynamics of Photoinduced Cell Plasma membrane injury.*
Rakestraw, Scott L. et al, PNAS, USA, vol. 87, pp. 4217-4221, Jun. 1990.*
Viti et al, Cancer Research, vol. 59, pp. 347-352, Jan. 15, 1999, Increased binding affinity and valence of Recombinant antibody fragments lead to improved targeting of tumoral angiogenesis.*

(Continued)

*Primary Examiner* — Christine J Saoud
*Assistant Examiner* — Jegatheesan Seharaseyon
(74) *Attorney, Agent, or Firm* — Millen, White, Zelano, Branigan, P.C.

(57) ABSTRACT

The present invention relates to antibodies with sub-nanomolar affinity specific for a characteristic epitope of the ED-B domain of fibronectin, a marker of angiogenesis. Furthermore, it relates to the use of radiolabelled high affinity anti ED-B antibodies for detecting new-forming blood vessels in vivo and a diagnostic kit comprising said antibody. Furthermore, it relates to conjugates comprising said antibodies and a suitable photoactive molecules (e.g. an appropriately chosen photosensitizer or radionuclide), and their use for the selective light-mediated occlusion of new blood vessels.

17 Claims, 21 Drawing Sheets

U.S. PATENT DOCUMENTS

| | | | |
|---|---|---|---|
| 7,273,924 B1 * | 9/2007 | Neri et al. | 530/387.1 |
| 7,320,786 B2 * | 1/2008 | Chen | 424/9.6 |
| 7,335,775 B2 | 2/2008 | Berger et al. | |
| 2003/0045681 A1 * | 3/2003 | Neri et al. | 530/350 |
| 2003/0046714 A1 * | 3/2003 | Simard et al. | 800/3 |
| 2003/0176663 A1 * | 9/2003 | Neri et al. | 530/388.22 |
| 2004/0001790 A1 | 1/2004 | Hilger et al. | |
| 2004/0013640 A1 * | 1/2004 | Zardi et al. | 424/85.1 |
| 2005/0074401 A1 * | 4/2005 | Borsi et al. | 424/1.49 |
| 2005/0112690 A1 * | 5/2005 | Heldmann | 435/7.1 |
| 2005/0142144 A1 * | 6/2005 | Simard et al. | 424/185.1 |
| 2005/0221434 A1 | 10/2005 | Menrad et al. | |
| 2005/0221440 A1 * | 10/2005 | Simard et al. | 435/69.3 |
| 2005/0260234 A1 * | 11/2005 | Simard et al. | 424/277.1 |
| 2006/0088530 A1 * | 4/2006 | Chen | 424/143.1 |
| 2006/0115428 A1 * | 6/2006 | Menrad et al. | 424/1.49 |
| 2007/0189963 A1 | 8/2007 | Neri et al. | |
| 2008/0274099 A1 * | 11/2008 | Neri et al. | 424/130.1 |
| 2009/0208410 A1 * | 8/2009 | Berndorff et al. | 424/1.49 |
| 2009/0214423 A1 * | 8/2009 | Borsi et al. | 424/1.49 |

FOREIGN PATENT DOCUMENTS

| | | |
|---|---|---|
| CA | 2385593 A1 | 4/2001 |
| EP | 0120694 | 10/1984 |
| EP | 0125023 | 11/1984 |
| EP | 184187 | 6/1986 |
| EP | 0211047 | 2/1987 |
| EP | 239400 | 9/1987 |
| EP | 344134 | 11/1989 |
| EP | 0371998 | 6/1990 |
| EP | 0396612 | 11/1990 |
| EP | 0396612 A1 | 11/1990 |
| EP | 0550400 | 7/1993 |
| EP | 0719790 A2 | 7/1996 |
| EP | 0731167 | 9/1996 |
| EP | 0760679 | 3/1997 |
| EP | 0760679 A1 | 3/1997 |
| EP | 1130099 A1 | 9/2001 |
| GB | 2188638 | 10/1987 |
| JP | 0276598 | 3/1990 |
| JP | 02076598 * | 3/1990 |
| JP | 4169195 | 6/1992 |
| JP | HEI4169195 * | 6/1992 |
| WO | WO 93/11161 | 6/1993 |
| WO | WO 94 09817 A | 5/1994 |
| WO | WO 94/13804 | 6/1994 |
| WO | WO 95/32001 | 11/1995 |
| WO | WO 95 32001 A1 | 11/1995 |
| WO | WO 96/23816 | 8/1996 |
| WO | 97/45544 * | 12/1997 |
| WO | WO 9745544 | 12/1997 |
| WO | WO9745544 | 12/1997 |
| WO | WO 99 51265 A1 | 10/1999 |
| WO | WO 9958570 | 10/1999 |
| WO | WO 99 58570 A2 | 11/1999 |
| WO | WO 01 23005 R | 11/2000 |
| WO | WO 01 23005 A1 | 4/2001 |
| WO | WO 0162800 | 8/2001 |
| WO | WO 01 96599 A2 | 12/2001 |
| WO | WO 03 055917 A2 | 7/2003 |
| WO | WO 03 076469 A2 | 9/2003 |

OTHER PUBLICATIONS

Tomohiko Fukuda et al., "Mice lacking the EDB segment of fibronectin develop normally but exhibit reduced cell growth and fibronectin matrix assembly in vitro," Cancer Research, Oct. 1, 2002, pp. 5603-5610, vol. 62.

Andrew Griffiths et al., "Isolation of high affinity human antibodies directly from large synthetic repertoires," The EMBO Journal, 1994, pp. 3245-3260, vol. 13, No. 14.

Dario Neri et al., "Targeting by affinity-matured recombinant antibody fragments of an angiogenesis associated fibronectin isoform", Nature Biotechnology, vol. 15, Nov. 1997, pp. 1271-1275.

Dario Neri et al., "Affinity reagents against tumour-associated extracellular molecules and newforming vessels," Advanced Drug Delivery Reviews, Apr. 6, 1998, pp. 43-52, vol. 31, No. 1-2, XP002124780, pp. 46, right-hand column, p. 49, left-hand column.

Pini, A., et al., "Design and use of a phage display library. Human antibodies with subnanomolar affinity against a marker of angiogenesis eluted from a two-dimensional gel," Journal of Biological Chemistry, Aug. 21, 1998, pp. 21769-21776, vol. 273, No. 34, XP002124781.

Viti F. et al., "Increased Binding Affinity and Valence of Recombinant Antibody Fragments Lead to Improved Targeting of Tumoral Angiogenesis," Cancer Research, Jan. 15, 1999, pp. 347-352, vol. 59, No. 2, XP002124782, the whole document.

R. Fattorusso et al., "NMR structure of the human oncofetal fibronectin ED-B domain, a specific marker for angiogenesis", Apr. 15, 1999, Structure, pp. 381-390, vol. 7, No. 4, XP002124783.

Tarli L et al., "A high-affinity human antibody that targets tumoral blood vessels," Blood, Jul. 1, 1999, pp. 192-198, vol. 94, No. 1, XP002124784.

M. Zalutsky et al., "Labeling monoclonal antibodies and F(ab')2 fragments with the alpha-particle-emitting nuclide astatine-211: preservation of immunoreactivity and in vivo localization," Proceedings of the National Academy of Sciences in the U.S.A., Sep. 1989, vol. 86, No. 18, pp. 7149-7153, XP002172060, Washington DC, USA, abstract.

S. Lindegren et al., "Chloramine-T in high-specific-activiity radioiodination of antibodies using N-succinimidyl-3-(trimehtylstannyl)benzoate as an intermediate," Nuclear Medicine and Biology, Oct. 1998, pp. 659-665, vol. 25, No. 7, XP004149436, Oxford, GB, abstract.

M. Birchler et al., "Selective targeting and photocoagulation of ocular angiogenesis mediated by a phage-derived human antibody fragment," Nature Biotechnology, Oct. 1999, pp. 984-988, vol. 17, No. 10, XP002172061, New York, NY, USA, the whole document.

Patrizia Castellani et al., "The Fibronectin isoform containing the ED-B Oncofetal domain: A marker of angiogensis," Int. J. Cancer, Dec. 1, 1994, pp. 612-618, vol. 54.

Luciano Zardi, et al., "Transformed human cells produce a new fibronectin isoform by preferential alternative splicing of a previously unobserved exon", The Embo Journal, vol. 6, No. 8, Aug. 1987, pp. 2337-2342.

Barbara Carnemolla, et al., "Phage antibodies with pan-species recognition of the oncofoetal angiogenesis marker fibronectin ED-B domain," International Journal of Cancer, vol. 68, No. 3, Nov. 4. 1996, pp. 397-405.

Zang, et al., "Antibody Specific for Extra Domain B of Fibronectin Demonstrates Elevated Levels of Both Extra B(+) and B(−) Fibronectin in Osteoarthritic Canine Cartilage" *Matrix Biology* vol. 14 (1994), pp. 623-633.

Peters, "Expression of the alternatively spliced EIIIB segment of fibronectin," Cell Adhesion and Communication, vol. 3, No. 1, pp. 67-89, 1995, XP002042097.

Camemolla, et al., "The Inclusion of the Type III Repeat ED-B in the Fibronectin Molecule Generates Conformationals That Unmask a Cryptic Sequence" The Journal of Biological Chemistry, (1992) vol. 267, No. 34, pp. 24689-24692.

Judah Folkman, "Angiogenesis in cancer, vascular, rheumatoid and other disease", Nature Medicine, vol. 1, No. 1, 1995, pp. 27-31.

Renata Pasqualini et al., "α-Vintegrins as receptors for tumor targeting by circulating ligands", Nature Biotechnology, vol. 15, Jun. 1997, pp. 542-546.

Michael S. O'Reilly et al., "Angiostatin induces and sustains dormancy of human primary tumors in mice", Nature Medicine, vol. 12, No. 6, Jun. 1996, pp. 689-692.

Xianming Huang et al., "Tumor Infarction in Mice by Antibody-Directed Targeting of Tissue Factor to Tumor Vasculature", Science, vol. 275, Jan. 24, 1997, pp. 547-550.

Dario Neri et al., "Biophysical methods for the determination of antibody-antigen affinities", Tibtech (vol. 14), Dec. 1996, pp. 465-470.

E. Sally Ward et al., Binding activities of a repetoire of singe immunoglobulin variable domains secreted from *Escherichia coli*, Nature, vol. 341, No. 6242, Oct. 12, 1989, pp. 544-546.

Robert E. Bird et al., "Single Chain Antigen-Binding Proteins", Science, vol. 242, Oct. 21, 1988, pp. 423-426.

James S. Huston, et al., "Protein engineering of antibody binding sites: Recovery of specific activity in an anti-digoxin single-chain Fv analogue produced in *Escherichia coli*", Proc. Natl. Acad. Sci. USA, vol. 85, Aug. 1988. pp. 5879-5883.

Philipp Holliger, et al., "'Diabodies': Small bivalent and bispecific antibody fragments", Proc. Natl. Acad. Sci. USA, vol. 90, Jul. 1993, pp. 6444-6448.

Philipp Holliger, et al., "Engineering bispecific antibodies", Current Opinion in Biotechnology, vol. 4. No. 4, 1993, pp. 446-449.

Dario Neri et al., "High-affinity Antigen Binding by Chelating Recombinant Antibodies (CRAbs)", Journal of Molecular Biology, vol. 246, No. 3, Feb. 4, 1995, pp. 367-373.

Cyrus Chothia, et al., "Canonical Structures for the Hypervariable Regions of Immunoglobulins", Journal of Molecular Biology, vol. 196, No. 4, Aug. 20, 1987, pp. 901-917.

D. Neri, et al, "Multipurpose High Sensitivity Luminescence Anaylzer (LUANA): Use in Gel Electrophoresis", Biotechniques, vol. 20, No. 4, Apr. 1996, pp. 708-712.

Ian M. Tomlinson, et al., "The Repertoire of Human Germline $V_H$ Sequence Reveals about Fifty Groups of $V_H$ Segments with Different Hypervariable Loops", Academic Press, vol. 227, No. 3, Oct. 5, 1992, pp. 776-798.

Johnathan P. L. Cox, et al, "A directory of human germ-line $V_x$ segments reveals a strong bias in their usage", European Journal of Immunology Apr. 1994, pp. 827-836.

James D. Marks, et al., "By-passing Immunization Human Antibodies from V-gene Libraries Displayed on Phage", Journal of Molecular Biology, vol. 222, No. 3, Dec. 5, 1991, pp. 581-597.

Tim Clarkson. et al., "Making antibody fragments using phage display libraries", Nature, vol. 352, Aug. 15, 1991, pp. 624-628.

Hennie R. Hoogenboom, et al., "Multi-subunit proteins on the surface of filamentous phage: methodologies for displaying antibody (FAB) heavy and light chains", Nucleic Acids Research, vol. 19, No. 15, Aug. 11, 1991, pp. 4133-4137.

Dario, Neri, et al., Radioactive labeling of recombinant antibody fragments by phosphorylation using human casein kinase II and [γ-$^{32}$P]-ATP, Nature Biotechnology, vol. 14, No. 4, Apr. 1996, pp. 485-490.

Robert Schier, et al., "Identification of functional and structural amino-acid residues by parsimonious mutagenesis" Gene, vol. 169, (1996), No. 2, pp. 147-155.

Wataru Ito, et al., "Mutations in the Complementarity-determining Regions do not cause Differences in Free Energy during the Process of Formation of the Activated Complex between an Antibody and the Corresponding Protein Antigen", Journal of Molecular Biology, vol. 248, No. 4, May 12, 1995, pp. 729-732.

C. Hamers-Casterman, et al., "Naturally occurring antibodies devoid of light chains", International Weekly Journal of Science, vol. 363, No. 6428, Jun. 3, 1993, pp. 446-448.

U. Jönsson, et al., "Real-Time Biospecific Interaction Analysis Using Surface Plasmon Resonance and a Sensor Chip Technology", Biotechniques, vol. 11, No. 5, Nov. 1991, pp. 620-627.

Ahuva Nissim, et al., "Antibody fragments from a 'single pot' phage display library as immunochemical reagents", The Embo Journal, vol. 13, No. 3, Feb. 1, 1994, pp. 692-698.

Aissandro Pini, et al., "Hierarchical affinity maturation of a phage library derived antibody for the selective removal of cytomegalovirus from plasma", Journal of Immunological Methods, vol. 206, Nos. 1-2, 1997, pp. 171-182.

Daniel R. Deaver, "A new non-isotopic detection system for immunoassays", Nature, vol. 377, No. 6551, Oct. 26, 1995, pp. 758-760.

Matsuura H., Takio K., Titani K., Greene T., Levery SB, Salyan ME, Hakomori S., J. Biol. Chem. 263, 3314-3322, "The oncofetal structure of human fibronectin defined by monoclonal antibody FDC-6. Unique structural requirement for the antigenic specificity provided by a glycosylhexapeptide", Mar. 1988. Abstract Only.

Zheng, M.et al., Int. J. Pept. Protein Res., 43, 230-8, "Synthetic immunochemistry of glycohexapeptide analogues characteristic of oncofetal fibronectin. Solid-phase synthesis and antigenic activity"; Mar. 1994. Abstract Only.

Feinberg, RF, Kliman HJ, Bedian V, Monzon-Bordonaba F, Menzin AW, Wang CL; Am. J. Obstet. Gynecol 172, 1526-1536; "Monoclonal antibody X18A4 identifies an oncofetal fibronectin eptiope distinct from the FDC-6 binding site"; May 1995. Abstract Only.

Paul K. Schick, Carol M. Wojenski, Vickie D. Bennett, and Tamara Ivanova; "The Synthesis and Localization of Alternatively Spliced Fibronectin EIIIB in Resting and Thrombin-Treated Megakaryocytes"; Blood, vol. 87, No. 5, Mar. 1, 1996; pp. 1817-1823.

Denise G. White, James W. Hall, David W. Brandli, Amy L. Gehris, and Vickie D. Bennett; "Chick Cartilage Fibronectin Differs in Structure from the Fibronectin in Limb Mesenchyme"; 1996; Exp. Cell Res. 224, pp. 391-402.

Database WPI Week 9017 Derwent Publications Ltd., London, GB; AN 90-128252 XP002042103 & JP 02 076 598 A (Fujita Gakuen et al.), Mar. 15, 1990.

Database WPI Week 9231 Derwent Publications Ltd., London, GB; AN 92-253398 XP002042104 & JP 04 169 195 A (Fujita Gakuen et al.), Jun. 17, 1992.

Ashley Publications Ltd., "Antibodies to the ED-B domain of fibronectin, their constructs and uses," Medical Research Council, ISSN 1354-3776, Patent Evaluation; WO 9745544; Exp. Opin. Ther. Patents (1998), 8(7):907-910.

Mariani et al., "Tumor Targeting Potential of the Monoclonal AntibodyvBC-1 against Oncofetal Fibronectin in Nude Mice Bearing Human Tumor Implants," The American Cancer Society, Dec. 15, 1997, pp. 2378-2384, vol. 80, No. 12.

Dario Neri et al., "Antibodies from, phage display libraries as immunochemical reagents," Methods in Molecular Biology, Immunochemical protocols, $2^{nd}$ ed., pp. 475-500, vol. 80.

Birchler et al., "Infrared photodetection for the in vivo localisation of phage-derived antibodies directed against angiogenic markers," Journal of Immunological Methods, 1999, pp. 239-248, vol. 231.

Fredrik Nilsson et al., "The use of phage display for the development of tumour agents," Advanced Drug Delivery Reviews, 2000, pp. 165-196, vol. 43.

Fredrik Nilsson et al., "Targeted Delivery of Tissue Factor to the ED-B Domain of Fibronectin, a Marker of Angiogenesis, Mediates the Infarction of Solid Tumors in Mice," Cancer Research, Jan. 15, 2001, pp. 711-716, vol. 61.

Halin et al., "Antibody-based targeting of Angiogenesis," Critical Reviews in Therapeutic Drug Carriers Systems, 2001, pp. 299-339, vol. 28, No. 3.

Leonardo Giovannoni et al., "Isolation of anti-angiogenesis antibodies from a large combinatorial repertoire by colony filter screening," Nucleic Acids Research, 2001, vol. 9, No. 5, e27.

Salvatore Demarti et al., "Selective targeting of tumour neovasculature by a radiohalogenated human antibody fragment specific for the ED-B domain of fibronectin," European Journal of Nuclear Medicine, Apr. 2001, short communication, vol. 28, No. 4.

Barbara Carnemolla et al., "Enhancement of the antitumor properties of interleukin-2 by its targeted delivery to the tumor blood vessel extracellular matrix," Hemostatis, Thrombosis, and Vascular Biology, Blood, Mar. 1, 2002, pp. 1659-1665, vol. 99, No. 5.

Halin et al., "Enhancement of the antitumor properties of interleukin-12 by its targeted delivery to the tumor blood vessel extracellular matrix," Nature Biotechnology, Mar. 2002, pp. 264-269, vol. 20.

C Marty et al., "Cytotoxic targeting of F9 teratocarcinoma tumours with anti-ED-B fibronectin scFv antibody modified liposomes," British Journal of Cancer, 2002, pp. 106-112, vol. 87, Cancer Research UK.

Samu Melkko et al., "An antibody-calmodulin fusion protein reveals a functioncal dependence between macromolecular isoelectric point and tumor targeting performance," Int. J. Radiation Oncology Biol. Phys., 2002, pp. 1485-1490, vol. 54, No. 5.

Patrizia Castellani et al., "Differentiation between High- and Low-Grade Astrocytoma Using a Human Recombinant Antibody to the Extra Domain-B of Fibronectin," American Journal of Pathology, Nov. 2002, 1695-1700, vol. 161, No. 5, American Society for Investigative Pathology.

L Borsi et al., "Selective Targeting of Tumoral Vasculature: Comparison of Different Formats of an Antibody (L19) to the ED-B Domain of fibronectin," Int. J. Cancer, 2002, pp. 75-85, vol. 102.

M Santimaria et al., "Immunoscintigraphic Detection of the ED-B Domain of Fibronectin, a Marker of Angiogenesis, in Patients with Cancer," Clinical Cancer Research, Feb. 2003, pp. 571-579, vol. 9.

J Scheuermann et al., "Discovery and ivestigation of lead compounds as binders to the extra-domain B of the angiogenesis marker, fibronectin," Drug Development Research, 2003, pp. 268-282, vol. 58.

Halin et al., "Synergistic therapeutic effects of a tumor targeting antibody fragment, fused to interleukin 12 and to tumor necrosis factor α," Cancer Research, Jun. 15, 2003, pp. 3202-3210, vol. 63.

L Borsi et al., "Selective targeted delivery of TNFα to tumor blood vessels," Blood First Edition Paper, prepublished online Aug. 21, 2003, American Society of Hematology, DOI 10.1182/blood-2003-04-1039.

M Nicolo et al., "Expression of Extradomain-B-containing Fibronectin in Subretinal Choroidal Neovascular Membranes," 2003, Elsevier Science Inc.

F Viti et al., "Recombinant antibodies for the selective targeting of tumor neovasculature," Current Opinion in Drug Discovery & Development, 2002, pp. 204-213, vol. 5, No. 2.

F Viti et al., "Phage display libraries as a source of tumour-targeting agents," Chimia, 2001, pp. 206-211, vol. 55, ISSN 0009-4293, The Academic Polymer Scene in Switzerland.

D Neri et al., Edited by P. Riva, "New Approaches to Tumour Targeting," Cancer Radioimmunotherapy: Present and Future, Nuclear Medicine Department, Hospital "M. Bufalini," Cesena, Italy, Harwood academic publishers.

M Birchler et al., "Expression of the extra domain B of fibronectin, a marker of angiogenesis, in head and neck tumors," Laryngoscope, Jul. 2003, pp. 1231-1237, vol. 113.

Alan L. Epstein, et al., "Identification of a Monoclonal Antibody, TV-1, Directed against the Basement Membrane of Tumor Vessels, and Its Use to Enhance the Delivery of Macromolecules to Tumors after Conjugation with Interleukin 2," Cancer Research 55, pp. 2673-2680, Jun. 15, 1995.

J Peters et al., "Fibronectin Isoform Distribution in the Mouse: II. Differential Distribution of the Alternatively Spliced EIIIB, EIIIA, and V Segments in the Adult Mouse," Cell Adhesion and Communication, 1996, pp. 127-148, vol. 4, No. 2.

Chevalier, X., et al., "Increased expression of Ed-B-Containing fibronectin (an embryonic isoform of fibronectin) in human osteoarthritic cartilage," British Journal of Rheumatology, vol. 35(5), pp. 407-415, (abstract only).

Chevalier, X., et al., "Presence of ED-A containing Fibronectin in human articular cartilage from patients with osteoarthritis and rheumatoid arthritis," Journal of Rheumatology, vol. 23(6), pp. 1022-1030, Jun. 1996.

Koukoulis, GK, et al., "Immunolocalization of cellular fibronectins in the normal liver, cirrhosis, and Hepatocellular carcinomea," Ultrastructural pathology, Jan.-Feb. 1995, vol. 19(1), pp. 37-43.

Moyano, JV, et al., "Fibronectin type III5 repeat contains a novel cell adhesion sequence, KLDAPT, which binds activated α4β1 and α4β7 integrins," Journal of Biological Chemistry, Oct. 3, 1997, vol. 272(40), pp. 24832-24836.

Yu, J L et al., "Fibronectin exposes different domains after adsorption to a heparinized and an unheparinized poly(vinyl chloride) surface," Biomaterial, Mar. 1997, vol. 18(56), pp. 421-427.

Borsi, L., et al., "Preparation of phage antibodies to the ED-A domain of human fibronectin," Exp. Cell Res., May 1, 1998, vol. 240(2), p. 244-251.

Kaczmarek, J et al., Int. J. Cancer, vol. 58, pp. 11-16, 1994.

Kirkham, PM et al., J. Mol. Biol., 1999, pp. 909-915, vol. 285.

Manage, Ri-Ichiroh et al., Journal of Cell Biology, vol. 139(1), pp. 295-307, Oct. 6, 1997.

Mardon, H J et al., Journal of Cell Science, vol. 104, pp. 783-792, 1993.

Menzin, A W et al. Cancer 1998, vol. 82, pp. 152-158.

Paolella, Giovanni E Tal, Nucleic acids research, vol. 16(8), pp. 3545-3557, 1988.

Staffa, A et al., The Journal of Biological Chemistry, 272(52), pp. 33394-33401, Dec. 1997.

Vartio, T et al., "Differential expression of the ED sequence-containing form of cellular fibronectin in embryonic and adult human tissues," Journal of cell science, vol. 88, pp. 419-430, 1987.

Ueda, Yasuo et al., "Selective Distribution of Fibronectin to a Tumor-Cell Line," Cancer Letters, vol. 31, pp. 261-265, 1986.

G Mariani et al., "A pilot pharmacokinetic and immunoscintigraphic study with the technetium-99m-labeled monoclonal antibody BC-1 directed against oncofetal fibronectin in patients with brain tumors," Cancer, Dec. 15, 1997, pp. 2484-2489, vol. 80, suppl. 12, ISSN: 0008-543X, Journal code: CLZ, abstract, USA.

Carnemolla et al., Journal of Cell Biology, vol. 108, pp. 1139-1148, 1989.

Harlow and Lane, (Antibodies, A laboratory Manual, Cold Springs Harbor Laboratory Publications, 1988).

Carter, et al. (Current Opinion in Biotechnology, 1997, 8, 449-454).

Office Action of May 15, 2009 in U.S. Appl. No. 11/637,810.

Office Action of Jul. 14, 2009 in U.S. Appl. No. 10/321,558.

Rudikoff, S., et al., "Single Amino Acid Substitution Altering Antigen-Binding Specificity," Proc. Natl. Acad. Sci. USA, vol. 79, pp. 1979-1983, Mar. 1982.

Neri, D., et al., "Antibodies from Phage Display Libraries as Immunochemical Reagents," Methods in Molecular Biology, Immunochemical Protocols, $2^{nd}$ Edition, pp. 475-500, vol. 80, 1998.

Alberts et al., "Cells Can Be Redesigned to Produce Proteins of Any Desired Sequence."(*Molecular Biology of the Cell*), 1984, 323-324, 3.

Argraves et al., "Amino Acid Sequence of the Human Fibronectin Receptor." (*Journal of Cell Biology*), 1987, 1183-1190, 105.

Batista et al., "The two membrane isoforms of human IgE assemble into functionally distinct b cell antigen receptors." (*The Journal of Experimental Medicine*), May 1, 1996, 2197-2205,184:6.

Bauters et al., "Accumulation of fetal fibronectin mRNAs after balloon denudation of rabbit arteries." (*Circulation*), 1995, 904-911, 92, pp. 904-911, 1995.

Berndorff et al., "Imaging of tumor angiogenesis using 99mTc-labeled human recombinant anti-ED-B fibronectin antibody fragments." (*Journal of Nuclear Medicine*), Oct. 2006, 1707-1716, 47:10.

Berndorff et al., "Radioimmunotherapy of Solid Tumors by Targeting Extra Domain B Fibronectin: Identification of Best-Suited Radioimmunoconjugate." (*Clinical Cancer Research*), 2005, 7053-7063, 11: Suppl. 19.

Bestagno et al., "Membrane Immunoglobulins Are Stabilized by Interchain Disulfide Bonds Occurring within the Extracellular Membrane-Proximal Domain." (Biochemistry), Sep. 4, 2001, 10686-10692, 40:35.

Blythe et al., "Benchmarking B-cell epitope prediction: Underperformance of existing methods." (*Protein Science*), 2005, 246-248,14.

Caldas et al., "Humanization of the anti-CD18 antibody 6.7: an unexpected effect of a framework residue in binding to antigen." (*Molecular Immunology*), May 2003, 941-952, 39:15.

Casset et al., "A peptide mimetic of an anti-CD-4 monoclonal antibody by rational design." (*Biochemical and Biophysical Research Communications*), 2003, 198-205, 307.

Castellani et al., "The Fibronectin Isoform Containing the ED-B Oncofetal Domain: A Marker of Angiogenesis." (*International Journal of Cancer*), Dec. 1, 1994, 612-618, 59:5.

Chien et al., "Significant structural and functional change of an antigen-binding site by a distant amino acid substitution: Proposal of a structural mechanism." (*Proc. Natl. Acad. Sci. USA*), Jul. 1989, 5532-5536, 86:14.

Chirivi et al., "Angiogenesis induced by alternatively spliced oncofetal fibronectin binding to endothelial cell integrin α3 β1." (*American Association for Cancer Research*), 2001. Abstract #14.

Colman et al., "Effects of amino acid sequence changes on antibody-antigen interactions." (*Research in Immunology*), 1994, 33-36, 145.

Dinkelborg et al., "Molecular imaging of atherosclerosis using a technetium-99m-labeled endothelin derivative." (*J. Nuclear Medicine*), 1998, 1819-1822, 39.

Epstein et al., "FDA Regulation of HIV-Related Tests and Procedures", *AIDS Testing: A Comprehensive Guide to Technical, Medical, Social, Legal, and Management Issues*, Eds. Schochetman and George, 52-61, Springer-Verlag, New York.

Ffrench-Constant et al., "Alternative splicing of fibronectin is temporally and spatially regulated in the chicken embryo." (*Development*) 1989, 375-388, 106.
Freshney et al., *Culture of Animal Cells: A Manual of Basic Technique*; . Alan R. Liss, Inc., New York, p. 4, 1983.
Folkman et al. "Angiogenesis in cancer, vascular, rheumatoid, and other disease." (*Nature Medicine*), 1995, 27-30, 1.
Garcia-Velasco et al., "Regulation of Monocyte Chemotactic Protein-1 Expression in Human Endometrial Stromal Cells by Integrin-Dependent Cell Adhesion." (*Biology Reproduction*), Aug. 1999, 548-552, 61:2.
George et al., "Radiometal labeling of recombinant proteins by a genetically engineered minimal chelation site: Technetium-99m coordination by single-chain Fv antibody fusion proteins through a C-terminal cysteinyl peptide." (*Proc. Natl. Acad. Sci.*) Aug. 1995, 8358-8362 92:18.
Giusti et al., "Somatic diversification of S107 from an antiphosphocholine to an anti-DNA autoantibody is due to a single base chain in its heavy chain variable region." (*Proc. Natl. Acad. Sci.*), May 1987, 2926-2930, 84:9.
Glukhova et al., "Expression of fibronectin variants in vascular and visceral smooth muscle cells in development." (*Developmental Biology*), Sep. 1990, 193-202, 141:1.
Goel et al., "99m Tc-Labeled Divalent and Tetravalent CC49 Single-Chain Fv's: Novel Imaging Agents for Rapid in vivo Localization of Human Colon Carcinoma." (*Journal of Nuclear Medicine*), Oct. 2001, 1519-1527, 42.
Greenspan et al., "Defining epitopes: It's not as easy as it seems." (*Nature Biotechnology*), 1999, 936-937, 17.
Gussow et al., "Humanization of Monoclonal Antibodies." (*Methods in Enzymology*), 1991, 99-121, 203.
Halin et al., "Antibody-based targeting of Angiogenesis Mediates the Infarction of Solid Tumors in Mice." (*Cancer Research*), Jan. 15, 2001, 711-716, 61.
Hashimoto-Uoshima et al., "The Alternatively Spliced Domains EIIIB and EIIIA of Human Fibronectin Affect Cell Adhesion and Spreading." (*Journal of Cell Science*), 1997, 2271-2280, 110:18.
Holm et al., "Functional mapping and single-chain construction of the anti-cytokeratin 8 monoclonal antibody TS1." (*Mol. Immunol.*), Feb. 2007, 1075-1084, 44:6.
Isemura et al., "Isolation and Characterization of Human Placenta Fibronectin." (*J. Biochem*), 1984, 163-169, 96.
Kaspar et al., "Fibronectin as Target for Tumor Therapy." (*Int. J. Cancer*), May 15, 2006, 1331-1339, 118:6.
Katugampola et al., "[$^{125}$I-His$^9$Ghrelin], a novel radioligand for localizing GHS orphan receptors in uhman and rat tissue: up regulation or receptors with atherosclerosis." (*British Journal of Pharmacology*), 2001, 143-149, 134.
Kern et al., "Interaction of Type IV Collagen with the Isolated Integrins α1 β1 and α2 β1." (*Eur. J. Biochem.*), 1993, 151-159, 215:a.
Kogan et al., "A Single Amino Acid Residue can Determine the Ligand Specificity of E-Selectin." (*J. Bio. Chem.*), 1995, 14047-14053, 270:23.
Korver et al., "Measurement of Primary In Vivo IgM- and IgG-Antibody Response to KLH in Humans: Implications of Pre-Immune IgM Binding in Antigen-Specific ELISA", (*Journal of Immunological Methods*), 1984, 241-251, 74.
Li et al., "Mammalian cell expression of dimeric small immune proteins (SIP)." (*Protein Engineering*), 1997 731-736, 10:6.
Liu et al., "Treatment of B-cell Lymphoma with Chimeric IgG and Single-Chain Fv Antibody-Interleukin-2 Fusion Proteins." (*Blood*), Sep. 15, 1998, 2103-2112, 92:6.
Maccallum et al., "Antibody-Antigen Interactions: Contact Analysis and Binding Site Topography." (*J. Mol. Biol.*), Oct. 11, 1996, 732-745, 262:5.
Magnusson et al., "Fibronectin: structure, assembly, and cardiovascular implications." (*Arteriosclerosis, Thrombosis, and Vascular Biology*), Sep. 1998, 1363-1370, 18:9.
Mariuzza et al., "The Structural Basis of Antigen-Antibody Recognition." (*Ann. Rev. Biophys. Biophys. Chem*), 1987, 139-159, 16.

Marty et al., "Production of functionalized single-chain Fv antibody fragments binding to the ED-B domain of the B-isoform of fibronectin in *Pichia pastoris*." (*Protein Expr Purif.*) Feb. 2001, 156-164, 21:1.
Matsuura et al., "An α-N-Acetyl Galactosaminylation at the Threonine Residue of a Defined Peptide Sequence Creates the Oncofetal Peptide Epitope in Human Fibronectin." (*The Journal of Biological Chemistry*), 1989, 10472-10476, 264:18.
Matsuura et al., "The oncofetal domain of fibronectin defined by monoclonal antibody FDC-6: Its presence in fibronectins from fetal and tumor tissues and its absence in those from normal adult tissues and plasma." (*Proc. Natl. Acad. Sci.*), 6517-6521, 82.
Menrad et al., "ED-B fibronectin as a target for antibody-based cancer treatments." (*Expert Opinion Therapeutic Targets*), 2005, 491-500, 9:3.
Morikawa et al., "Radioimmunoassay for TA-0910, a new stable thryotropin releasing hormone analogue and its metabolite, TA-0910 acid type, in human plasma and urine." (*Journal of Pharmaceutical and Biomedical Analysis*), 1998, 1267-1274, 16.
Ngo et al., "Computational Complexity, Protein Structure Prediction, and the Levinthal Paradox in the Protein Folding Problem," Chapter 14 of *The Protein Folding Problem and Tertiary Structure Prediction*, Birkhauser, 1994, 435-508.
Nozawa et al., "HMMC-1: A Humanized Monoclonal Antibody With Therapeutic Potential Against Mullerian Duct-Related Carcinomas." (*Clinical Cancer Research*), Oct. 15, 2004, 7071-7078, 10.
Office Action of Final Rejection filed on Apr. 21, 2004 issued in U.S. Appl. No. 10/321,558.
Office Action of Final Rejection filed on Dec. 5, 2008 issued in U.S. Appl. No. 10/321,558.
Office Action of Final Rejection filed on Jun. 21, 2006 issued in U.S. Appl. No. 10/336,041.
Office Action of Final Rejection filed on May 15, 2009 issued in U.S. Appl. No. 11/637,810.
Office Action of Final Rejection filed on Nov. 13, 2007 issued in U.S. Appl. No. 10/321,558.
Office Action of Final Rejection filed on Nov. 14, 2007 issued in U.S. Appl. No. 10/336,041.
Office Action of Final Rejection filed on Nov. 27, 2009 issued in U.S. Appl. No. 10/336,041.
Office Action of Final Rejection filed on Oct. 18, 2006 issued in U.S. Appl. No. 10/088,866.
Office Action of Final Rejection filed on Oct. 31, 2007 issued in U.S. Appl. No. 10/966,097.
Office Action of Final Rejection filed on Sep. 1, 2005 issued in U.S. Appl. No. 10/088,866.
Office Action of Final Rejection filed on Sep. 12, 2008 issued in U.S. Appl. No. 10/088,866.
Office Action of Non-Final Rejection filed on Apr. 9, 2007 issued in U.S. Appl. No. 10/966,097.
Office Action of Non-Final Rejection filed on Aug. 6, 2007 issued in U.S. Appl. No. 10/088,866.
Office Action of Non-Final Rejection filed on Dec. 12, 2007 issued in U.S. Appl. No. 11/105,475.
Office Action of Non-Final Rejection filed on Dec. 17, 2008 issued in U.S. Appl. No. 10/966,097.
Office Action of Non-Final Rejection filed on Feb. 1, 2006 issued in U.S. Appl. No. 10/088,866.
Office Action of Non-Final Rejection filed on Feb. 18, 2005 issued in U.S. Appl. No. 10/088,866.
Office Action of Non-Final Rejection filed on Jan. 8, 2009 issued in U.S. Appl. No. 10/321,558.
Office Action of Non-Final Rejection filed on Jul. 14, 2009 issued in U.S. Appl. No. 10/321,558.
Office Action of Non-Final Rejection filed on Jun. 22, 2006 issued in U.S. Appl. No. 10/088,866.
Office Action of Non-Final Rejection filed on Jun. 25, 2004 issued in U.S. Appl. No. 10/321,558.
Office Action of Non-Final Rejection filed on Jun. 29, 2009 issued in U.S. Appl. No. 10/088,866.
Office Action of Non-Final Rejection filed on Jun. 3, 2008 issued in U.S. Appl. No. 11/105,475.

Office Action of Non-Final Rejection filed on Mar. 18, 2009 issued in U.S. Appl. No. 10/336,041.

Office Action of Non-Final Rejection filed on Mar. 5, 2007 issued in U.S. Appl. No. 10/336,041.

Office Action of Non-Final Rejection filed on May 30, 2007 issued in U.S. Appl. No. 10/321,558.

Office Action of Non-Final Rejection filed on Oct. 1, 2008 issued in U.S. Appl. No. 11/637,810.

Office Action of Non-Final Rejection filed on Sep. 22, 2005 issued in U.S. Appl. No. 10/336,041.

Orlova et al, "Comparative Biodistribution of the radiohalogenated (Br, I and At) antibody A33. Implications for in vivio dosimetry." (*Cancer Biotherapy and Radiopharmaceuticals*), 2002, 385-396, 17:4.

Pascalis et al., "Grafting of 'abbreviated' complementarity-determining regions containing specific-determining residues essential for ligand contact to engineer a less immunogenic humanized monoclonal antibody." (*Journal of Immunology*), 2002, 3076-3084, 169.

Pasqualini et al., "α-V integrins as receptors for tumor targeting by circulating ligands." (*Nature Biotechnology*), Jun. 1997, 542-546, 15.

Poon et al., "Laser-Induced Fluorescence: Experimental Intraoperative Delineation of Tumor Resection Margins." (*J. Neurosurgery*), 1992, 679-686, 76:4.

Rudikoff et al., "Single amino acid substitution altering antigen-binding specificity." (*Proc. Natl. Acad. Sci. USA*), Mar. 1982, 1979-1983, 79.

Schier et al., "Isolation of Picomolar Affinity Anti-c-erbB-2 Single-chain Fv by Molecular Evolution of the Complementarity Determining Regions in the Center of the Antibody Binding Site." (*J. Molecular Biology*), 1996, 551-567, 263.

Swiss-Prot accession No. A2KBB9 dated Feb. 20, 2007, Anti-ED-B scFV antibody, from Pini et al. "Design and use of a phage display library." (*Journal Biol. Chem.*) see: EMBL; AJ006111; CAA06862.1; -; mRNA.

Swiss-Prot accession No. A2KBC0 dated Feb. 20, 2007, Anti-ED-B scFV antibody, from Pini et al. "Design and use of a phage display library." (*Journal Biol. Chem.*) see: EMBL; AJ006112; CAA06863.1; -; mRNA.

Swiss-Prot accession No. A2KBC2 dated Feb. 20, 2007, Anti-ED-B scFV antibody, from Pini et al. "Design and use of a phage display library." (*Journal Biol. Chem.*) see: EMBL; AJ006114; CAA06865.1; -; mRNA.

Swiss-Prot accession No. A2KBC3 dated Feb. 20, 2007, Anti-ED-B scFV antibody, from Pini et al. "Design and use of a phage display library." (*Journal Biol. Chem.*) see: EMBL; AJ006115; CAA06866.1; -; mRNA.

Swiss-Prot accession No. A2KBC1 dated Feb. 20, 2007, Anti-ED-B scFV antibody, from Pini et al. "Design and use of a phage display library." (*Journal Biol. Chem.*) see: EMBL; AJ006113; CAA06864.2; -; mRNA.

Tait et al., "Development and Characterization of Annexin V Mutants with Endogenous Chelation Sites for Tc." (*Bioconjugate Chem.*), 2000, 918-925, 11.

Takada et al., "The Primary Structure of the VLA-2/Collagen Receptor Alpha2 Subunit (Platelet GPIA): Homology to Other Integrins and the Presence of a Possible Collagen-Binding Domain." (*Journal of Cell Biology*), Jul. 1, 1989, 397-407, 109:1.

U.S. Appl. No. 10/088,866, filed Jul. 2, 2002.

Vajdos et al., "Comprehensive functional maps of the antigen-binding site of an anti-ErbB2 antibody obtained with shotgun scanning mutagenesis." (*Journal of Molecular Biology*), 2002, 415-428, 320.

Vangelista et al., "A minimal receptor Ig chimera of human FcεRI α-chain efficiently binds secretory and member IgE." (*Protein Engineering*), Jan. 2002, 51-57, 15:1.

Wagner et al., "Differentiation of Polymorphonuclear Neutrophils in Patients with Systemic Infections and Chronic Inflammatory Diseases: Evidence of Prolonged Life Span and de novo Synthesis of Fibronectin." (*Journal of Molecular Medicine*), 2000, 337-345, 78:6.

Weir et al., "An Immunoglobulin G1 Monoclonal Antibody Highly Specific to the Wall of Cryptosporidium Oocysts." (*Clinical and Diagnostic Laboratory Immunology*), Sep. 2000, 745-750, 7:5.

Wilson et al., "Simvastatin Preserves the Structure of Coronary Adventitial Vasa Vasorum in Experimental Hypercholesterolemia Independent of Lipid Lowering."(*Circulation*), Jan. 29, 2002 415-418, 105:4.

Winkler et al., "Changing the Antigen Binding Specificity by Single Point Mutations of an Anti-p24 (HIV-1) Antibody." (*J. Immun.*), 2000, 4505-4514, 265.

Wu et al., "High-resolution microPET imaging of carcino-embryonic antigen-positive xenografts by using a copper-64-labeled engineered antibody fragment." (*National Academy of Science*), Jul. 18, 2000, 8495-8500, 97:15.

Yang et al., "CDR Walking Mutagenesis for the Affinity Maturation of a Potent Human Anti-HIV-1 Antibody into the Picomolar Range." (*Journal of Molecular Biology*), 1995, 392-403, 254.

Zalutsky et al., "Astatine-211-labeled radiotherapeutics: An emerging approach to targeted alpha-particle radiotherapy." (*Current Pharmaceutical Design*), Sep. 2000, 1433-1455, 6.

Zhang et al., "Non-invasive imaging of atherosclerotic plaque macrophage in a rabbit model with F-18 FDG PET: a histopathological correlation." (*BMC Nuclear Medicine*), 2006, 1-7, 25.

Chen, et al., "Adhesion Mediated by Fibronectin's Alternatively Spliced $ED_b$ (EIIIB) and Its Neighboring Tyoe III Repeats," Experimental Cell Research 223, 9-19 (1996), Article No. 0053.

Kim, et al., "Regulation of Angiogenesis in Vivo by Ligation of Integrin α5β1 with the Central Cell-Binding Domain of Fibronectin," American Journal of Pathology, Bol. 156, No. 4, Apr. 2000, pp. 1345-1362.

Glockshuber, R., et al., "A Comparison of Strategies to Stabilize Immunoglobulin $F_v$-Fragments," Biochemistry 1990, 29, 1362-1367.

Office Action issued Apr. 13, 2011 in U.S. Appl. No. 10/321,558, filed Dec. 18, 2002, 15 pages.

* cited by examiner

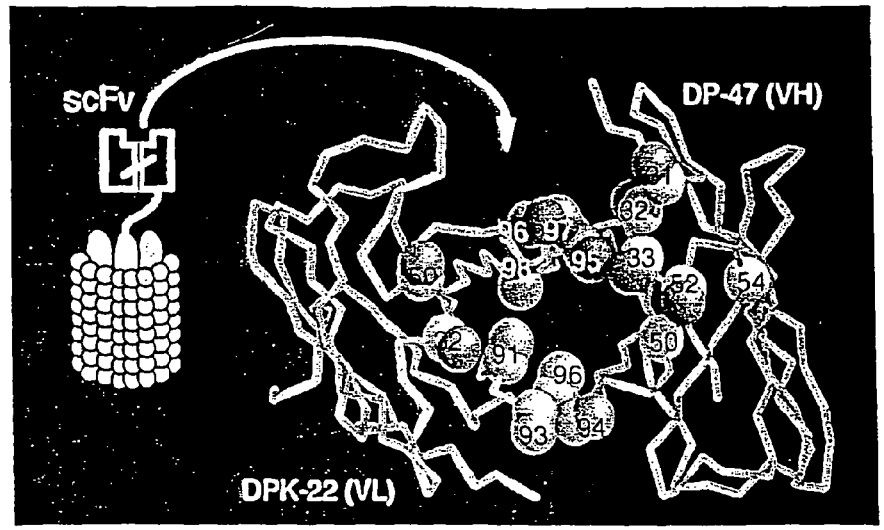

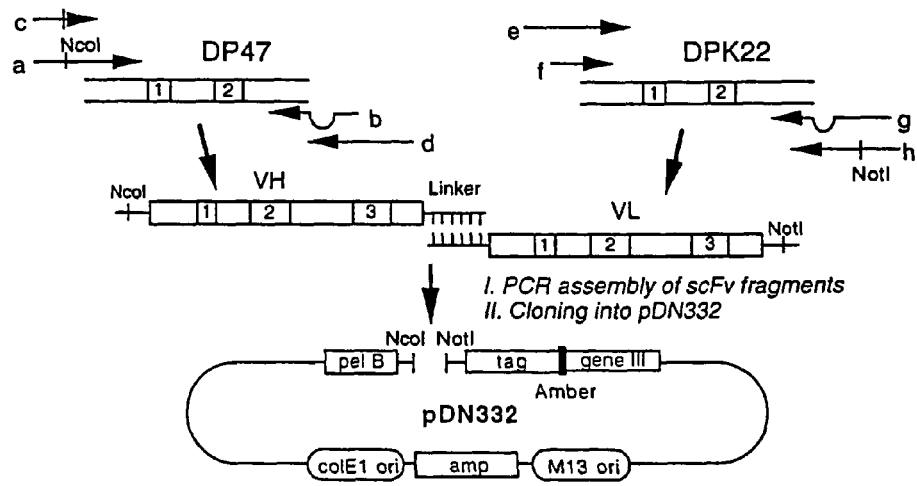

| | VH primers: | |
|---|---|---|
| a | DP47baNco | GCG GCC CAG CAT GCC ATG GCC GAG GTG CAG CTG TTG GAG TCT GGG |
| b | CDR3for | GGT TCC CTG GCC CCA GTA GTC AAA MNN MNN MNN MNN TTT CGC ACA GTA ATA TAC G |
| c | VHpullth | GCG GCC CAG CAT GCC ATG GCC GAG |
| d | Jassm | CCC GCT ACC GCC ACT GGA CCC ATC GCC ACT CGA GAC GGT GAC CAG GGT TCC CTG GCC CCA GTA GTC |
| | VL primers: | |
| e | DPK22assm | GAT GGG TCC AGT GGC GGT AGC GGG GGC GCG TCG ACT GGC GAA ATT GTG TTG ACG CAG TCT CC |
| f | DPK3for | CAC CTT GGT CCC TTG GCC GAA CGT MNN CGG MNN MNN ACC MNN CTG CTG ACA GTA ATA CAC TGC |
| g | Jfornot | GAG TCA TTC TCG ACT TGC GGC CGC TTT GAT TTC CAC CTT GGT CCC TTG GCC GAA CG |
| h | pullth | GAT GGG TCC AGT GGC GGT AGC GGG |

Figure 1

| %ID/g time (h) | scFv (L19) | | | | | | | scFv (D1.3) | |
|---|---|---|---|---|---|---|---|---|---|
| | Kidney | Spleen | Lung | Liver | Brain | Blood | Tumor | Blood | Tumor |
| 0.25 | 26.4 ± 4.7 | 5.4 ± 0.4 | 15.1 ± 5.1 | 5.7 ± 0.6 | 0.4 ± 0.04 | 14.4 ± 2.6 | 4.6 ± 1.0 | 12.7 ± 0.1 | 4.4 ± 0.4 |
| 1 | 19.2 ± 3.9 | 3.8 ± 0.3 | 9.8 ± 0.9 | 2.8 ± 0.3 | 0.3 ± 0.1 | 8.3 ± 0.9 | 6.9 ± 2.4 | 5.7 ± 0.7 | 3.6 ± 1.0 |
| 3 | 8.1 ± 1.6 | 2.0 ± 0.3 | 5.0 ± 1.4 | 1.7 ± 0.02 | 0.2 ± 0.01 | 4.3 ± 0.3 | 8.2 ± 4.2 | — | — |
| 5 | 4.2 ± 1.1 | 1.8 ± 0.2 | 3.5 ± 0.2 | 1.3 ± 0.3 | 0.1 ± 0.02 | 2.0 ± 1.6 | 7.7 ± 2.5 | 4.6 ± 1.2 | 2.6 ± 1.5 |
| 24 | 0.7 ± 0.1 | 0.4 ± 0.1 | 1.0 ± 0.1 | 0.2 ± 0.04 | 0.02 ± 0.01 | 0.4 ± 0.1 | 4.7 ± 0.6 | 1.1 ± 0.5 | 0.7 ± 0.4 |

day 9 / rabbit 1 / left / nC
day 9 / rabbit 1 / right / VEGF high
day 9 / rabbit 2 / left / PMA
day 9 / rabbit 2 / left / VEGF low
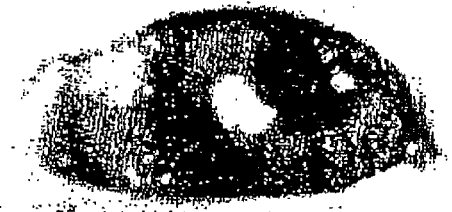
day 9 / rabbit 3 / left / VEGF high
day 9 / rabbit 3 / right / PMA
day 9 / rabbit 4 / left / PMA
day 9 / rabbit 4 / right / nC
Figure 6

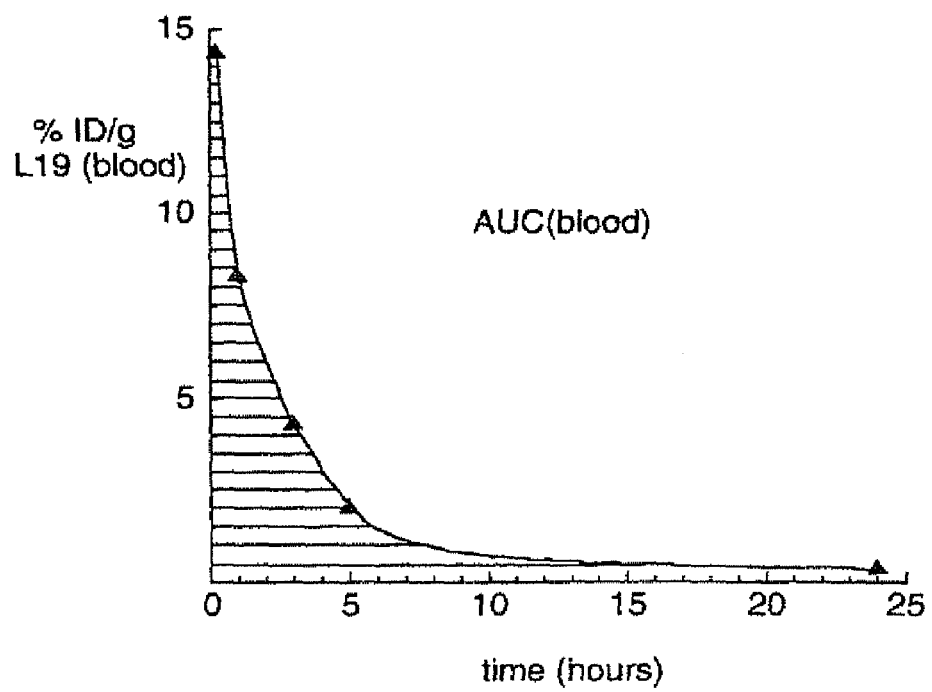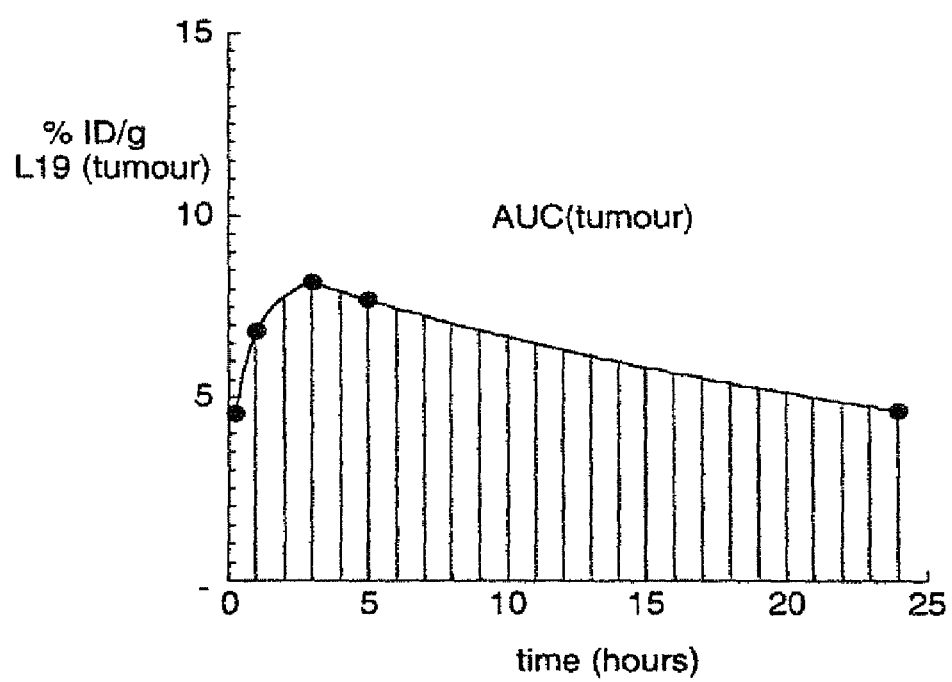
Figure 12

$^1$H-NMR spectrum of 3-(trimethylstannyl)-benzoic acid in CDCl$_3$

Figure 16b
1H-NMR spectrum of 3-(trimethylstannyl)-benzoic acid in CDCl$_3$
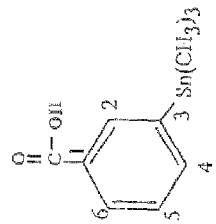
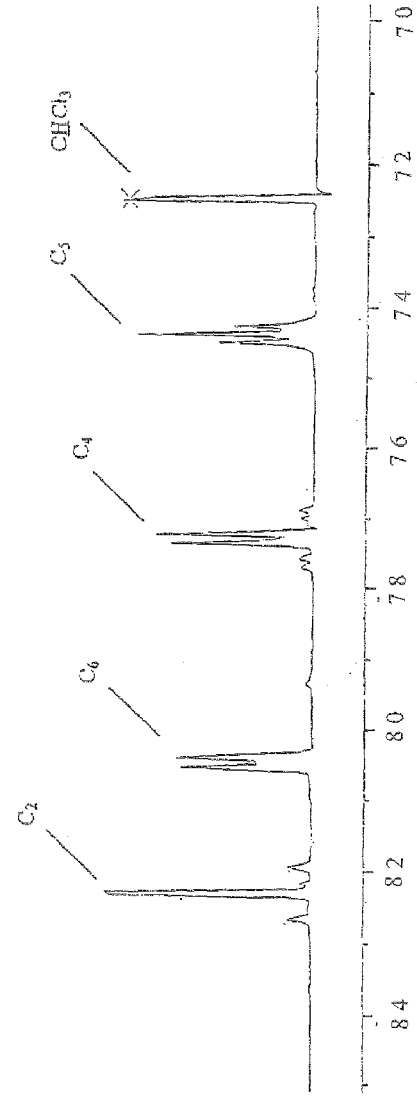

$^1$H-NMR spectrum of N-succinimidyl-3-(trimethylstannyl)-benzoate in $CDCl_3$ $^1$H-NMR spectrum of N-succinimidyl-3-(trimethylstannyl)-benzoate in CDCl$_3$

SEQUENCE LISTING

<160> NUMBER OF SEQ ID NOS: 34

<210> SEQ ID NO 1
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
gcggcccagc cggccatggc cgag                                              24

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other

<400> SEQUENCE: 2
gagcctggcg gacccagctc atmnnmnnmn ngctaaaggt gaatccagag gctg             54

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgagctggg tccgccaggc tcc                                               23

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other

<400> SEQUENCE: 4
gtctgcgtag tatgtggtac cmnnactacc mnnaatmnnt gagacccact ccagccccett      60

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
acatactacg cagactccgt gaag                                        24

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcattctcga cttgcggccg ctttgatttc caccttggtc ccttggccga acg        53

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other

<400> SEQUENCE: 7
gtttctgctg gtaccaggct aamnngctgc tgctaacact ctgactg               47

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttagcctggt accagcagaa acc                                         23

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, t, g, unknown or other

<400> SEQUENCE: 9
gccagtggcc ctgctggatg cmnnatagat gaggagcctg ggagcc                46

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcatccagca gggccactgg c                                           21

<210> SEQ ID NO 11
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggcccagc atgccatggc cgaggtgcag ctgttggagt ctggg                45

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other

<400> SEQUENCE: 12
ggttccctgg ccccagtagt caaamnnmnn mnnmnntttc gcacagtaat atacg      55

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggcccagc atgccatggc cgag                                        24

<210> SEQ ID NO 14
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccgctaccg ccactggacc catcgccact cgagacggtg accagggttc cctggcccca  60
gtagtc                                                            66

<210> SEQ ID NO 15
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatgggtcca gtggcggtag cggggggcgcg tcgactggcg aaattgtgtt gacgcagtct  60
```

-continued cc                                                             62

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other

<400> SEQUENCE: 16
caccttggtc ccttggccga acgtmnncgg mnnmnnaccm nnctgctgac agtaatacac    60
tgc                                                                 63

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagtcattct cgacttgcgg ccgctttgat ttccaccttg gtcccttggc cgaacg        56

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatgggtcca gtggcggtag cggg                                          24

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      H antibody specific for ED-B domain of fibronectin

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 20

<400> SEQUENCE: 20

000

<210> SEQ ID NO 21

<400> SEQUENCE: 21

000

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide formula

<400> SEQUENCE: 22

Glu Gly Ile Pro Ile Phe Glu Asp Phe Val Asp Ser Ser Val Gly Tyr
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide formula

<400> SEQUENCE: 23

Tyr Thr Val Thr Gly Leu Glu Pro Gly Ile Asp Tyr Asp Ile Ser
 1               5                  10                  15

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide formula

<400> SEQUENCE: 24

Asn Gly Gly Glu Ser Ala Pro Thr Thr Leu Thr Gln Gln Thr
 1               5                  10

<210> SEQ ID NO 25
<211> LENGTH: 72
<212> TYPE: DNA
<213> ORGANISM: Artificial Sequence
<220> FEATURE:
<223> OTHER INFORMATION: Description of Artificial Sequence: Synthetic
      DNA construct
<220> FEATURE:
<221> NAME/KEY: CDS
```

<222> LOCATION: (10)..(69)

<400> SEQUENCE: 25

```
gcggccgca gat gac gat tcc gac gat gac tac aag gac gac gac aag     51
          Asp Asp Asp Ser Asp Asp Asp Tyr Lys Asp Asp Asp Lys
          1               5                   10 cac cat cac cat cac cat tag                                        72
His His His His His His
15                  20
```

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 26

```
Asp Asp Asp Ser Asp Asp Asp Tyr Lys Asp Asp Asp Lys His His
1               5                   10                  15

His His His His
            20
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 27

```
Ala Ile Ser Gly Ser Gly
1               5
```

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 28

```
Ser Ile Arg Gly Ser Ser
1               5
```

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 29

```
Gly Leu Ser Ile
1
```

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      anti-ED-B antibody clone

```
<400> SEQUENCE: 30

Ser Phe Ser Phe
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 31

Phe Pro Phe Tyr
1

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 32

Asn Gly Trp Tyr Pro Trp
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 33

Gly Gly Trp Leu Pro Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      anti-ED-B antibody clone

<400> SEQUENCE: 34

Thr Gly Arg Ile Pro Pro
1               5
```

SPECIFIC BINDING MOLECULES FOR SCINTIGRAPHY, CONJUGATES CONTAINING THEM AND THERAPEUTIC METHOD FOR TREATMENT OF ANGIOGENESIS This application is a continuation of U.S. application Ser. No. 09/512,082 filed Feb. 24, 2000 now abandoned, which is a Continuation-in-Part of U.S. application Ser. No. 09/300,425, filed Apr. 28, 1999 now abandoned, which is a Continuation-in-Part of U.S. application Ser. No. 09/075,338, filed May 11, 1998 now abandoned.

SEQUENCE LISTING

The instant application contains a Sequence Listing which has been submitted via EFS-Web and is hereby incorporated by reference in its entirety. Said ASCII copy, created on Apr. 2, 2010, is named ELLIS000.txt and is 10,942 bytes in size.

FIELD OF THE INVENTION

The present invention relates to antibodies with sub-nanomolar affinity specific for a characteristic epitope of the ED-B domain of fibronectin, a marker of angiogenesis. It also relates to the use of radiolabelled high-affinity anti-ED-B antibodies for detecting new-forming blood vessels in vivo and a diagnostic kit comprising said antibody.

Moreover, the invention refers to conjugates comprising the above said antibodies and a suitable photoactive molecule (e.g., a photosensitizer) and to their use in the detection and/or coagulation of new blood vessels.

BACKGROUND OF THE INVENTION

Tumours cannot grow beyond a certain mass without the formation of new blood vessels (angiogenesis), and a correlation between microvessel density and tumour invasiveness has been reported for a number of tumours (Folkman (1995). Nature Med., 1, 27-31). Moreover, angiogenesis underlies the majority of ocular disorders which result in loss of vision [Lee et al., Surv. Ophthalmol. 43, 245-269 (1998); Friedlander, M. et al., Proc. Natl. Acad. Sci. U.S.A. 93, 9764-9769 (1996).]. Molecules capable of selectively targeting markers of angiogenesis would create clinical opportunities for the diagnosis and therapy of tumours and other diseases characterised by vascular proliferation, such as diabetic retinopathy and age-related macular degeneration. Markers of angiogenesis are expressed in the majority of aggressive solid tumours and should be readily accessible to specific binders injected intravenously (Pasqualini et al. (1997). Nature Biotechnol., 15, 542-546; Neri et al. (1997), Nature Biotechnol., 15 1271-1275). Targeted occlusion of the neovasculature may result in tumour infarction and collapse (O'Reilly et al. (1996). Nature Med., 2, 689-692; Huang et al. (1997). Science, 275, 547-550).

The ED-B domain of fibronectin, a sequence of 91 aminoacids identical in mouse, rat and human, which is inserted by alternative splicing into the fibronectin molecule, specifically accumulates around neo-vascular structures (Castellani et al. (1994). Int. J. Cancer 59, 612-618) and could represent a target for molecular intervention. Indeed, we have recently shown with fluorescent techniques that anti-ED-B single-chain Fv antibody fragments (scFv) accumulate selectively in tumoural blood vessels of tumour-bearing mice, and that antibody affinity appears to dictate targeting performance (Neri et al. (1997). Nature Biotechnol., 15 1271-1275; International Patent Application No. PCT/GB97/01412, based on GB96/10967.3). Tumour targeting was evaluated 24 hours after injection, or at later time points.

Various attempts are known in the art to raise antibodies against the ED-B-domain in order to use them for tumour targeting.

Peters et al. (Cell Adhesion and Communication 1995, 3: 67-89) disclose polyclonal antibodies raised to antigens containing no FN sequence other than the intact ED-B domain and show that they bind specifically and directly to this domain.

However, the reagents of Peters et al. suffer from a series of drawbacks:—the antisera of Peters et al. recognise ED-B(+)-FN only after treatment with N-glycanase. This makes these reagents unsuitable for applications such as tumour targeting, imaging and therapy, as deglycosylation cannot be performed in vivo.

The authors acknowledge themselves that their antibodies do not recognise full-length ED-B(+)-FN produced by mammalian cells. They also acknowledge that it had been impossible to produce monoclonal antibodies specific for the ED-B domain of fibronectin, even though antibodies against other domains of fibronectin (such as ED-A) had been produced. It is well-known in the art that polyclonal antisera are unacceptable for above mentioned applications.

Even after years of intense research in this field, monoclonal antibodies recognising the ED-B domain of fibronectin without treatment with N-glycanase could be produced only using phage display techniques as applied in the present invention.

Zang et al. (Matrix Biology 1994, 14: 623-633) disclose a polyclonal antiserum raised against the canine ED-B domain. The authors do expect a cross-reactivity to human ED-B(+)-FN, although this was not tested. However, the authors acknowledge the difficulty to produce monoclonal antibodies directly recognising the ED-B domain of fibronectin (page 631). The antiserum recognises ED-B(+)-FN in Western blot only after treatment with N-glycanase. As mentioned before, glycanase treatment renders these reagents unsuitable for applications according to the present invention.

Recognition of ED-B(+)-FN in ELISA proceeds without the need of deglycosylation but only on cartilage extracted with a denaturing agent (4M Urea) and captured on plastic using gelatin. The authors comment that "the binding of the FN molecule to the gelatine bound on the plastic surface of the ELISA plate may somehow expose the epitopes sufficiently for recognition by the antiserum". Since for in vivo applications FN cannot be denatured and gelatin bound, the monoclonal binders of the present invention offer distinct advantages.

The Japanese patents JP02076598 and JP04169195 refer to anti-ED-B antibodies. It is not clear from these documents if monoclonal anti ED-B antibodies are described. Moreover, it seems impossible that a single antibody (such as the antibody described in JP02076598) has "an antigen determinant in amino acid sequence of formulae (1), (2) or (3):

(1) EGIPIFEDFVDSSVGY (SEQ ID NO: 22)
(2) YTVTGLEPGIDYDIS (SEQ ID NO: 23)
(3) NGGESAPTTLTQQT (SEQ ID NO: 24)

on the basis of the following evidence:

i) A monoclonal antibody should recognize a well-defined epitope.

ii) The three-dimensional structure of the ED-B domain of fibronectin has been determined by NMR spectroscopy. Segments (1), (2) and (3) lie on opposite faces of the ED-B structure, and cannot be bound simultaneously by one monoclonal antibody.

Furthermore, in order to demonstrate the usefulness of the antibodies localisation in tumours should be demonstrated, as well as evidence of staining of ED-B(+)-FN structures in biological samples without treatment with structure-disrupting reagents.

The BC1 antibody described by Carnemolla et al. 1992, J. Biol. Chem. 267, 24689-24692, recognises an epitope on domain 7 of FN, but not on the ED-B domain, which is cryptic in the presence of the ED-B domain of fibronectin. It is strictly human-specific. Therefore, the BC1 antibody and the antibodies of the present invention show different reactivity. Furthermore, the BC1 antibody recognises domain 7 alone, and domain 7-8 of fibronectin in the absence of the ED-B domain (Carnemolla et al. 1992, J. Biol. Chem. 267, 24689-24692). Such epitopes could be produced in vivo by proteolytic degradation of FN molecules. The advantage of the reagents according to the present invention is that they can localise on FN molecules or fragments only if they contain the ED-B domain.

For the diagnosis of cancer, and more specifically for imaging primary and secondary tumour lesions, immunoscintigraphy is one of the techniques of choice. In this methodology, patients are imaged with a suitable device (e.g., a gamma camera), after having been injected with radiolabelled compound (e.g., a radionuclide linked to a suitable vehicle). For scintigraphic applications, short-lived gamma emitters such as technetium-99m, iodine-123 or indium-111 are typically used, in order to minimise exposure of the patient to ionising radiations.

The most frequently used radionuclide in Nuclear Medicine Departments is technetium-99m (99 mTc), a gamma emitter with half-life of six hours. Patients injected with 99 mTc-based radiopharmaceuticals can typically be imaged up to 12-24 hours after injections; however, accumulation of the nuclide on the lesion of interest at earlier time points is desirable.

Furthermore, if antibodies capable of rapid and selective localisation on newly-formed blood vessels were available, researchers would be stimulated to search for other suitable molecules to conjugate to antibodies, in order to achieve diagnostic and/or therapeutic benefit.

SUMMARY OF THE INVENTION

Considering the need of nuclear medicine for radiopharmaceuticals capable of localising tumour lesions few hours after injection, and the information that antibody affinity appears to influence its performance in targeting of angiogenesis, it is an object of the present invention to produce antibodies specific for the ED-B domain of fibronectin with sub-nanomolar dissociation constant (for a review on the definitions and measurements of antibody-antigen affinity, see Neri et al. (1996). Trends in Biotechnol. 14, 465-470). A further object of the present invention is to provide radiolabelled antibodies in suitable format, directed against the ED-B domain of fibronectin, that detect tumour lesions already few hours after injection.

In one aspect of the invention these objects are achieved by an antibody with specific affinity for a characteristic epitope of the ED-B domain of fibronectin and with improved affinity to said ED-B epitope.

In a further aspect of the present invention the above described antibody is used for rapid targeting markers of angiogenesis.

Another aspect of the present invention is a diagnostic kit comprising said antibody and one or more reagents for detecting angiogenesis.

Still a further aspect of the present invention is the use of said antibody for diagnosis and therapy of tumours and diseases which are characterized by vascular proliferation.

Finally, an important aspect of the invention is represented by conjugates comprising said antibodies and a suitable photoactive molecules (e.g. a judiciously chosen photosensitizer), and their use for the selective light-mediated occlusion of new blood vessels.

Terminology

Throughout the application several technical expressions are used for which the following definitions apply.

antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv; dAb, Fd; and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced. As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. It has been shown that fragments of a whole antibody can perform the function of binding antigens. Examples of binding fragments are (I) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature,), 341, 544-546.) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a polypeptide linker which allows the two domains to associate to form an antigen binding site (Bird et al. (1988) Science, 242, 423-426; Huston et al. (1988) Proc. Natl. Acad. Sci. U.S.A., 85, 5879-83.); (viii) bispecific single chain FV dimers (PCT/US92/09965) and (ix) "diabodies", multivalent or multispecific fragments constructed by gene fusion (WO94/13804; Holliger et al. (1993) Proc. Natl. Acad. Sci. U.S.A., 90, 6444-6448). Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). Where bispecific antibodies are to be used, these may be conventional bispecific antibodies, which can be manufactured in a variety of ways Holliger and Winter (1993), Curr. Opin. Biotech., 4, 446-449), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single-chain CRAbs described by Neri et al. ((1995) J. Mol. Biol., 246, 367-373).

complementarity-determining regions

Traditionally, complementarity-determining regions (CDRs) of antibody variable domains have been identified as those hypervariable antibody sequences, containing residues essential for specific antigen recognition. In this document, we refer to the CDR definition and numbering of Chothia and Lesk (1987) J. Mol. Biol., 196, 901-917.

functionally equivalent variant form

This refers to a molecule (the variant) which although having structural differences to another molecule (the parent) retains some significant homology and also at least some of the biological function of the parent molecule, e.g. the ability to bind a particular antigen or epitope. Variants may be in the form of fragments, derivatives or mutants. A variant, derivative or mutant may be obtained by modification of the parent molecule by the addition, deletion, substitution or insertion of one or more aminoacids, or by the linkage of another molecule. These changes may be made at the nucleotide or protein level. For example, the encoded polypeptide may be a Fab fragment which is then linked to an Fc tail from another source. Alternatively, a marker such as an enzyme, fluorescein, etc, may be linked. For example, a functionally equivalent variant form of an antibody "A" against a characteristic epitope of the ED-B domain of fibronectin could be an antibody "B" with different sequence of the complementarity determining regions, but recognising the same epitope of antibody "A".

We have isolated recombinant antibodies in scFv format from an antibody phage display library, specific for the ED-B domain of fibronectin, and recognising ED-B(+)-fibronectin in tissue sections. One of these antibodies, E1, has been affinity matured to produce antibodies H10 and L19, with improved affinity. Antibody L19 has a dissociation constant for the ED-B domain of fibronectin in the sub-nanomolar concentration range.

The high-affinity antibody L19 and D1.3 (an antibody specific for an irrelevant antigen, hen egg lysozyme) were radio-labelled and injected in tumour-bearing mice. Tumour, blood and organ biodistributions were obtained at different time points, and expressed as percent of the injected dose per gram of tissue (% ID/g). Already 3 hours after injection, the % ID/g (tumour) was better than the % ID/g (blood) for L19, but not for the negative control D1.3. The tumour:blood ratios increased at longer time points. This suggests that the high-affinity antibody L19 may be a useful tumour targeting agent, for example for immunoscintigraphic detection of angiogenesis.

photosensitizer (or photosensitiser)

A photosensitiser could be defined as a molecule which, upon irradiation and in the presence of water and/or oxygen, will generate toxic molecular species (e.g., singlet oxygen) capable of reacting with biomolecules, therefore potentially causing damage to biological targets such as cells, tissues and body fluids.

Photosensitisers are particularly useful when they absorb at wavelengths above 600 nm. In fact, light penetration in tissues and body fluids is maximal in the 600-900 nm range [Wan et al. (1981) Photochem. Photobiol. 34, 679-681).

The targeted delivery of photosensitisers followed by irradiation is an attractive avenue for the therapy of angiogenesis-related diseases [Yarmush, M. L. et al. Antibody targeted photolysis. *Crit. Rev. Therap. Drug Carrier Systems* 10, 197-252 (1993); Rowe, P. M. *Lancet* 351, 1496 (1998); Levy, J. *Trends Biotechnol.* 13, 14-18 (1995)), particularly for the selective ablation of ocular neovasculature. Available therapeutic modalities such as laser photocoagulation, either directly or after administration of photosensitising agents, are limited by a lack of selectivity and typically result in the damage of healthy tissues and vessels [Macular Photocoagulation Study Group, *Arch. Ophtalm.* 112, 480488 (1994); Haimovici, R. et al., *Curr. Eye Res.* 16, 83-90 (1997); Schmidt-Erfurth, U. et al.; *Graefes Arch. Clin. Exp. Ophthalmol.* 236, 365-374 (1998).].

On the basis of the arguments presented above, one can see that it would be extremely important to discover ways to improve the selectivity and specificity of photosensitisers, for example by conjugating them to a suitable carrier molecule. It is likely that the development of good-quality carrier molecules will not be a trivial task. Moreover, it is likely that not all photosensitisers will lend themselves to be "vehicled<< in vivo to the site of interest. Factors such as photosensitiser chemical structure, solubility, lipophilicity, stickiness and potency are likely to crucially influence the "targetability<< (and efficacy of photosensitisers' conjugates.

Here we show that the high-affinity L19 antibody, specific for the ED-B domain of fibronectin selectively localises to newly formed blood vessels in a rabbit model of ocular angiogenesis upon systemic administration. The L19 antibody, chemically coupled to the photosensitising agent tin (IV) chlorin $e_6$ and irradiated with red light, mediated the selective occlusion of ocular neovasculature and promoted apoptosis of the corresponding endothelial cells. These results demonstrate that new ocular blood vessels can be distinguished immunochemically from pre-existing ones in vivo, and strongly suggest that targeted delivery of photosensitisers followed by irradiation may be effective in treating blinding eye diseases and possibly other pathologies associated with angiogenesis.

Another important feature to be considered when conjugates containing a photosensitisers are used is the fact that photosensitisers are among the few species capable of mediating their toxic activity in the immediate proximity of the antibody to which they have been conjugated.

Upon irradiation and in the presence of oxygen, most photosensitisers produce, among other reactive species, singlet oxygen: a diffusive toxic molecule capable of damaging cells by reacting with membranes, proteins and DNA. The average diffusion of singlet oxygen has been estimated to be around 200 nm (Yarmush et al. 1993, Crit. Rev. Ther. Drug, 10, 197-252).

The same applies to alpha-emitting radionuclides, such as astatine-211, bismuth-212 and bismuth-213, which produce energetic alpha particles having a range in tissue penetration of 50-100 μM (Hauck et al. 1998, Brit. J. Cancer 77, 753-759), depositing energy that is about 500 times greater than that of beta particles, e.g. yttrium-90 (100 KeV/μM vs. 0.2 KeV/μM, respectively) (McDevitt et al. 1998, Eur. J. Nucl. Med. 25, 1341-135).

Photosensitisers or alpha-emitting radionuclides conjugated to the antibodies specific for the ED-B domain of fibronectin described in the present application, as for example L 19, can be targeted to new blood vessels in vivo, as illustrated in the examples hereinafter reported. Thanks to this exquisite specificity of localisation and to the short range of action of the toxic species released by photosensitiser and alpha-emitting radionuclides, specific damage can be inferred in the immediate proximity of the labelled antibody, while sparing adjacent tissues/cells.

Toxic species with a short path of action (such as singlet oxygen and alpha particles), when delivered by the L19 antibody, offer the possibility to selectively damage the endothelial cells of new blood vessels, while sparing normal tissues and blood cells. This level of selectivity should offer tremendous advantages for the control of angiogenesis-related disorders, such as cancer, rheumatoid arthritis, neo-vasculature associated ocular disorders and psoriasis.

The innovative concept of delivering short-range acting toxic agents to new blood vessels, while sparing established blood vessels and normal tissues, can be easily appreciated in the light of the following considerations.

Let us consider the biodistribution studies performed in tumour-bearing mice injected with radiolabelled L19, described in Example 3. When using the L19 antibody labelled with a beta-particle emitting radionuclide (e.g., Yttrium-90), the antibody delivers beta particles to the neighbouring cells/tissues with a penetration of several millimetres. Let us assume that all tissues in the body are equally radiosensitive, let us neglect radioactive decay, and let us remember that radioactivity will begin to exhibit its biocidal effect from the moment the radiolabelled antibody is injected intravenously (i.e., from time=0 s). The therapeutic advantage of the radiolabelled antibody will be related to the ratio between the total dose of radioactivity delivered by the antibody to the tumour and the total dose of radioactivity delivered by the antibody to blood or organs, normalised per gram of fluid or tissue (Behr et al. 1998, Int. J. Cancer 77, 787-795).

Let us examine the biocidal dose delivered to the tumour and to blood (representative of myelotoxicity, which is typically the limiting toxicity with radiolabelled antibodies).

The dose of radioactivity delivered per gram of tumour is proportional to the area under the curve (AUC) of the % ID/g (tumour), plotted versus time. Analogously, the dose of radioactivity delivered to blood is proportional to the area under the curve (AUC) of the % ID/g (blood), plotted versus time. During the first 24 hours after intravenous injection the ratio of AUC (tumour)/AUC (blood) is equal to 3.6 (FIG. 12). This ratio may somewhat increase when the AUCs are measured for longer time periods, but therapeutic ratios greater than 6-7 are rarely achieved. Let us now consider the situation in which a short-range-acting toxic species (e.g., a photosensitiser or an alpha-particle emitting radionuclide) is delivered to the tumoural blood vessels, and is therefore not homogenously distributed in the tumour mass. The diffusive toxic species (e.g., singlet oxygen or an alpha particle) will hardly penetrate more than one layer of cells, i.e. will hit only the endothelial cells lining the tumour blood vessel wall. Since new-forming blood vessels in most tumours (including the F9 teratocarcinoma) constitute less than 2% of the total tumour mass, the relevant parameter for predicting therapeutic benefit will be the ratio AUC(vessel)/AUC(blood).

As we can see in FIG. 13, L19 accumulates only around new blood vessels. This observation has also been confirmed by microautoradiographic analysis in tumours (Tarli et al. 1999, Blood, 94, 192-198). Since the radioactivity delivered to tumours is concentrated around neo-vascular structures, and assuming that tumoural vasculature accounts for 2% or the tumour weight, we can calculate that AUC (vessel)=($^{100}$/$_{2}$)×AUC (tumour)=50×AUC (tumour). In other words, the selectivity of the treatment is expected to be proportional to the ratio AUC (vessel)/AUC (blood), which is >150:1 over a period of 24 hours in our experimental system (see also FIG. 14 for explanation).

Let us consider astatine-211 as a particularly interesting alpha-particle emitting radionuclide for biomedical application. The half-life of its radioactive decay is considerably longer than the ones of bismuth-212 and bismuth-213 (7.2 hrs, compared to 1.0 hr and 45 min., respectively) (Larsen and Bruland 1998, Brit. J. Cancer 77, 1115-1122). Astatine is the heaviest halogen and no stable isotopes of this element exist. Since it is directly below iodine in the periodic table, it might be expected that the two halogens would possess similar chemical properties. However, attempts to label proteins with $^{211}$At by direct electrophilic astatination at the level of the protein aminoacid did not give successful results because of rapid loss of label following in vivo administration (Vaughan et al. 1978, Int. J. Nucl. Med. 5, 229-230). To circumvent this problem, L19 can be conjugated with $^{211}$At with significant nuclide incorporation and no loss of antibody specificity by the two-step labeling method published by Garg (Garg et al. 1989, Appl. Radiat. Isot. 40, 485-490). It involves the use of a bifunctional chemical compound, N-succinimidyl-3-(trimethylstannyl)-benzoate (m-MeATE; ATE, <<alkyltin ester>>) (Zalutsky et al. 1989, Proc. Natl. Acad. Sci; USA 86, 7149-7153), which we synthesized following the protocol published by Garg (see FIG. 15) as reported in Example 7.

It is important to report that using equimolar amount of m-bromobenzoic acid and trimethylstannyl-chloride, the reaction product is 3-(trimethylstannyl)benzoic acid rather than the published trimethylstannyl-3-(trimethylstannyl) benzoate. Based on the results of the labeling experiments, described below, we believe that this compound may have superior qualities compared to the previously described trimethylstannyl-3-(trimethylstannyl) benzoate derivatives.

The bifunctional m-MeATE agent can be used both to label L19 with the gamma-emitting iodine-125 and the alpha-emitting astatine-211 in a two-step methodology. Protein labeling with iodine-125 through m-MeATE rather than conventional electrophilic methods (e.g, the chloramine-T and the Iodogen methods) is reported to provide protein iodination sites which are more inert towards dehalogenation in vivo (Garg et al. 1989, Appl. Radiat. Isot. 40, 485-490). The labeling protein coupling efficiency together with the conjugate immunoreactivity arising from this two-step radiolabeling methodology were studied through the reaction with iodine-125.

In the first step, m-MeATE and t-buthylhydroperoxide (TBHP) were added to Na$^{125}$I. Following a 20 minutes incubation period, the radioiodinated product N-succinimidyl-3-($^{125}$I)-benzoate was isolated and separated from unconjugated m-MeATE by chromatography using a disposable silica gel Sep-Pak column and a gradient of ethyl acetate in hexane as eluent phase. Starting from 100 µCi of Na$^{125}$I, we coupled 90 µCi of $^{125}$I to the N-succinimidyl benzoate. A solution of L19 in borate buffer (pH 8.5) was added in the second step to the purified N-succinimidyl-3-($^{125}$I)-benzoate. Following an incubation time of 30 minutes on ice, the radiolabelled L19 was separated from unincorporated iodine using a PD-10 disposable gel filtration column. The resulting efficiency of L19 labeling using radioiodinated ATE resulted to be strongly dependent on initial protein concentration. Using L19 at a concentration of 0.42 µg/µl and 1 µg/µl, 18% and 28% of starting radiolabelled benzoate was coupled to L19, respectively. According to these results, if we started from 1 mCi of Na$^{125}$I and a concentration of L19 of 1 μg/μl, we would obtain L19 labelled with $^{125}$I at a specific activity of 1 μCi/μl. The initial concentration of L19 did not influence the immunoreactivity of the conjugates after labeling. Following the method reported in example 3, the immunoreactivity, defined as reported by Viti et al. (Viti et al. 1999, Cancer Research 59, 347-352) resulted to be in both cases >90%.

These results demonstrate the feasibility of the labeling of L19 with radiohalogens using the bifunctional m-MeATE.

Astatine-211 may offer the additional advantage that it is likely to be detached from L19 by dehalogenases in the kidney glomeruli (T. M. Behr et al. 1999, Cancer Res. 59, 2635-43), but not in tumoural vessels, therefore reducing kidney toxicity of the radiolabelled compound in spite of the clearance of the immunoconjugate via the renal route. For photosensitisers, glomeruli in the kidneys will not be damaged, since for most applications irradiation of the kidneys is not foreseen.

It is obviously also possible to prepare conjugates consisting of the antibody linked to a photosensitiser and a radionucleotide in order to take advantages of the activity of both.

DNA encoding antibody scFv L-19 has been deposited on Sep. 25, 2008, in ATCC (Manassas, Va.), and has accession no. PTA-9529.

BRIEF DESCRIPTION OF THE DRAWINGS

Embodiments of the present invention are illustrated by the following figures, wherein FIG. 1 shows a designed antibody phage library. "VH primers" are disclosed as SEQ ID NOS 11-14, respectively, in order of appearance. "VL primers" are disclosed as SEQ ID NOS 15-18, respectively, in order of appearance;

FIG. 6 shows rabbit eyes with implanted pellet;

FIG. 12 shows schematic diagrams in which the % of injected dose delivered per gram, respectively of blood and tumour, are plotted versus time.

FIGS. 16a and 16b report the 1H-NMR spectrum of 3-(trimethylstannyl)-benzoic acid.

DETAILS

FIG. 1 shows:

Designed antibody phage library. FIG. 1A Antibody fragments are displayed on phage as pIII fusion, as schematically depicted. In the antibody binding site (antigen's eye view), the Vk CDRs backbone and the VH CDR backbone are shown. Residues subject to random mutation are Vk CDR3 positions 91, 93, 94 and 96, and VH CDR3 positions 95, 96, 97, and 98. The Cb atoms of these side chains are shown in darker shades. Also shown (in grey), are the residues of CDR1 and CDR2, which can be mutated to improve antibody affinity. Using the program RasMol (Chemistry Department website at U.C.S.C.) the structure of the scFv were modeled from pdb file 1igm (Brookhaven Protein Data Bank; European Bioinformatics Institute website). FIG. 1B PCR amplification and library cloning strategy. The DP47 and DPK22 germline templates were modified (see text) to generate mutations in the CDR3 regions. Genes are indicated as rectangles, and CDRs as numbered boxes within the rectangle. The VH and the VL segments were then assembled and cloned in pDN332 phagemid vector. Primers used in the amplification and assembly are listed at the bottom.

Figure 2A:
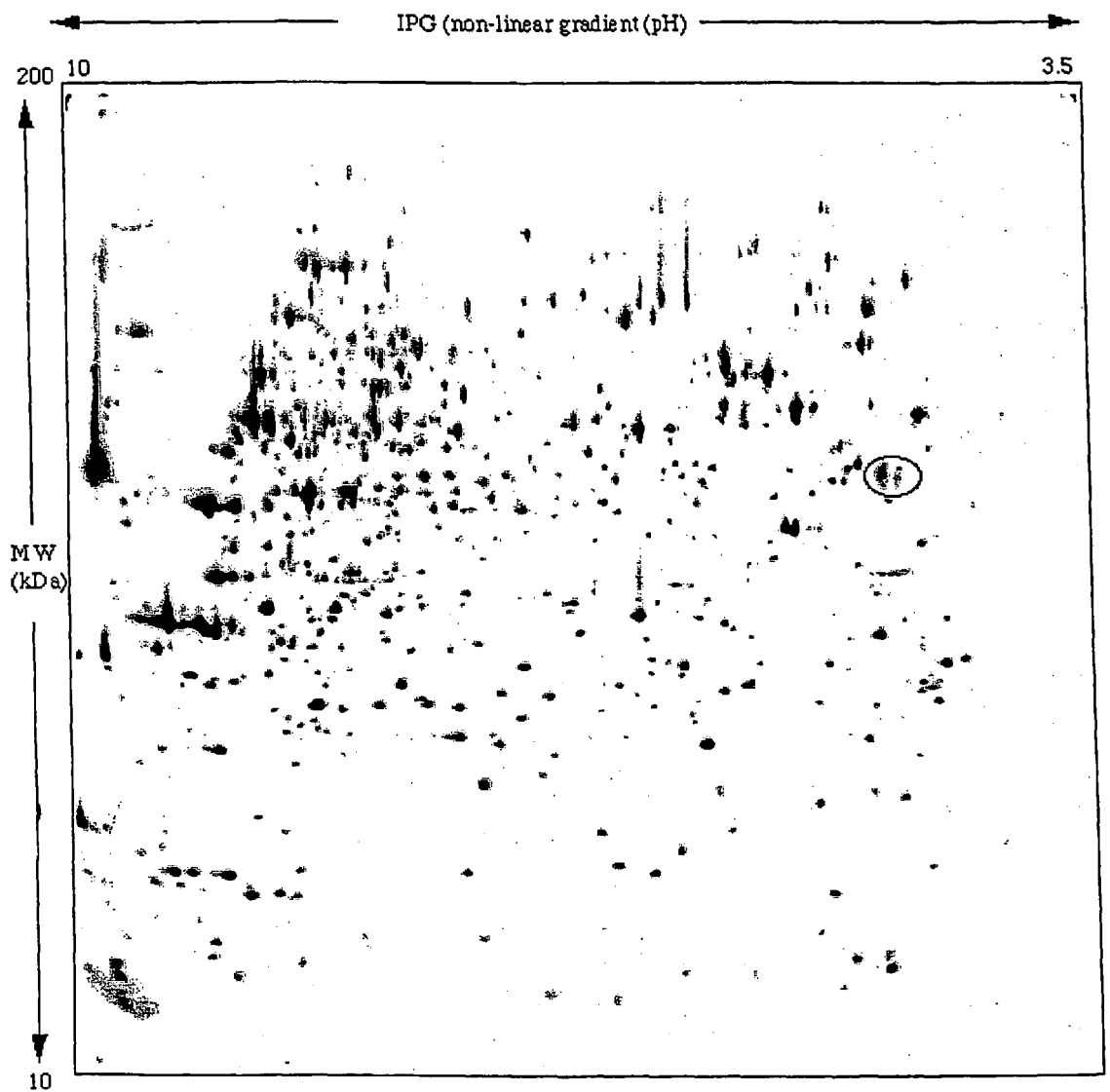
FIG. 2 shows 2D gels and Western blotting of a lysate of human melanoma COLO-38 cells.
Figure 2B:
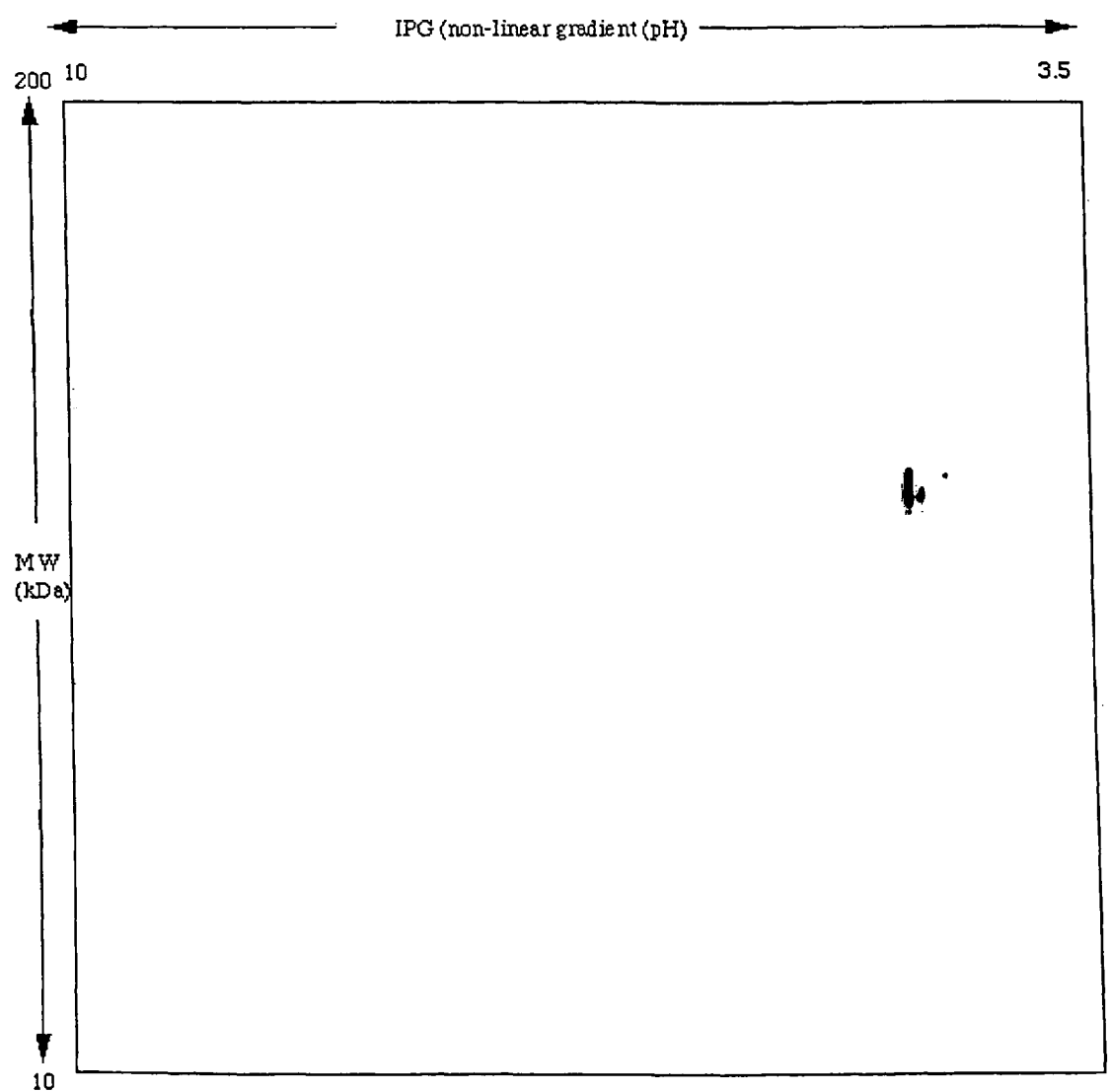

FIG. 2 shows 2D gels and western blotting (a) Silver-staining of the 2D-PAGE of a lysate of human melanoma COLO-38 cells, to which recombinant ED-B-containing 7B89 had been added. The two 7B89 spots (circle) are due to partial proteolysis of the His-tag used for protein purification. (b) Immunoblot of a gel, identical to the one of FIG. 2a, using the anti-ED-B E1 and the M2 anti-FLAG antibodies as detecting reagent. Only the 7B89 spots are detected, confirming the specificity of the recombinant antibody isolated from a gel spot.

Figure 3:
FIG. 3 shows immunohistochemical experiments of glioblastoma multiforme
Figure 4:
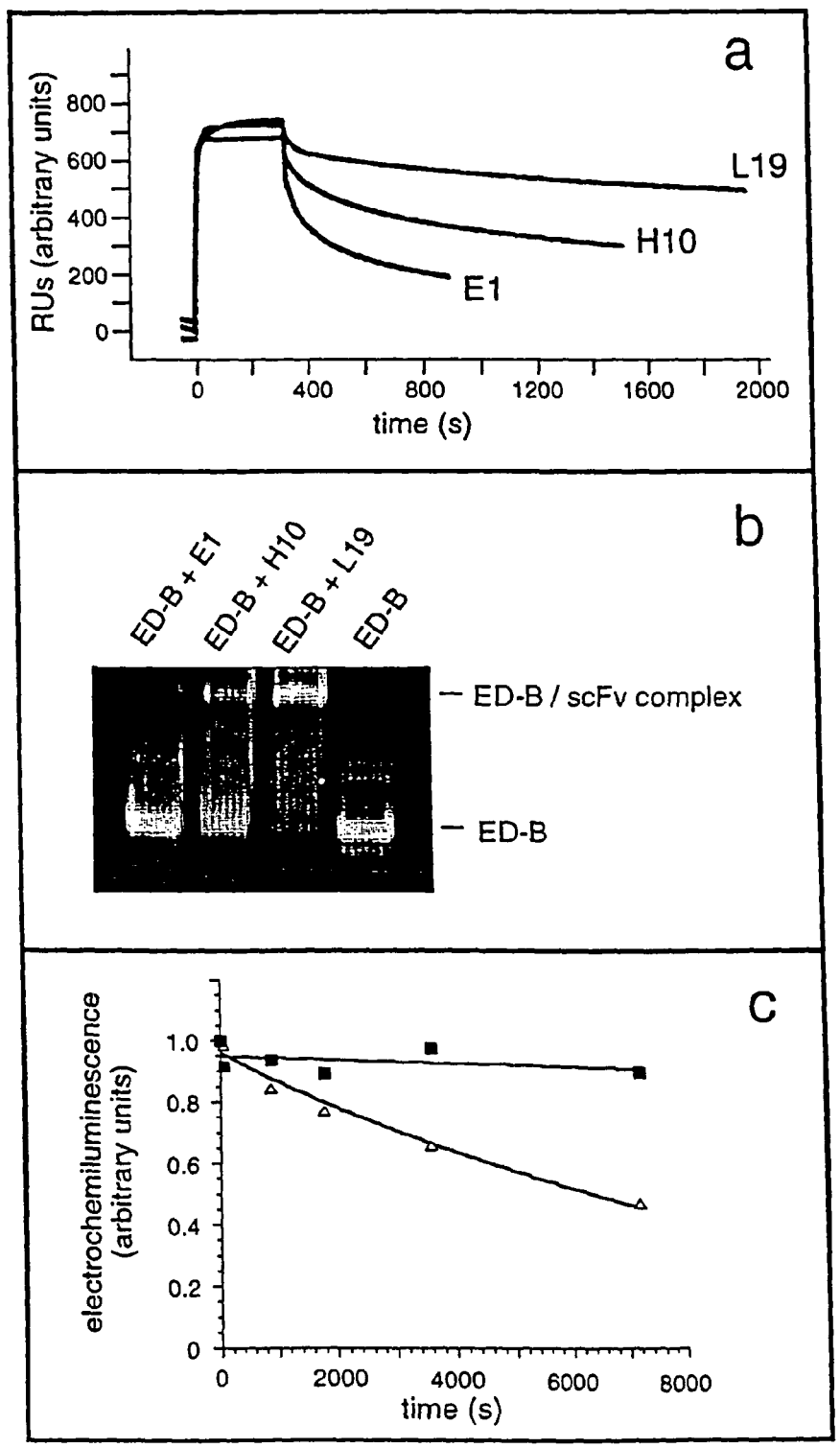
FIG. 4 shows an analysis of the stability of antibody-(ED-B) complexes.
Figure 5:
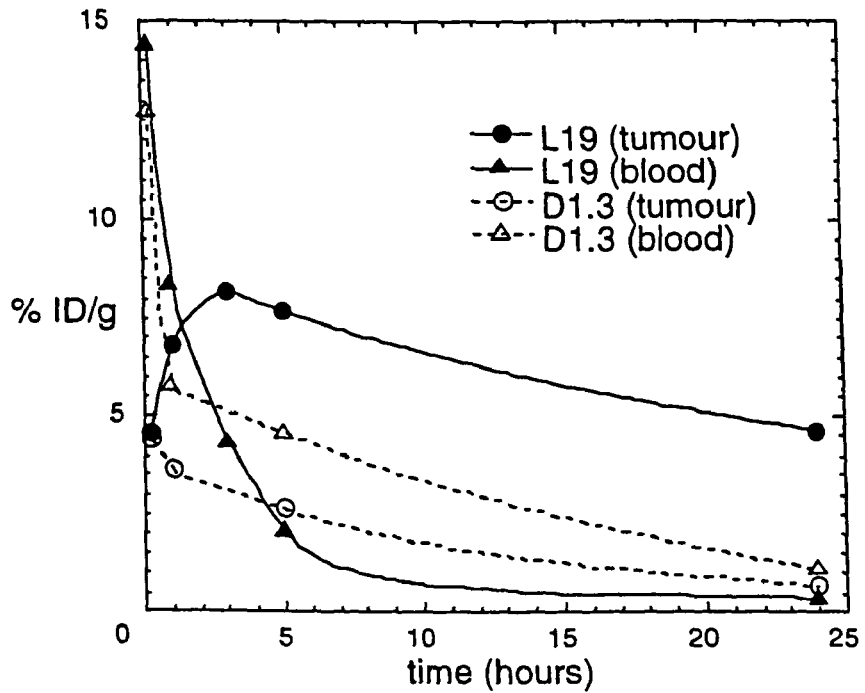
FIG. 5 shows biodistribution of tumour bearing mice injected with radiolabelled antibody fragments.

FIG. 3 shows:

Immunohistochemical experiments on serial sections of glioblastoma multiforme showing the typical glomerulus-like vascular structures stained using scFvs E1 (FIG. 3A), A2 (FIG. 3B), and G4 (FIG. 3C). Scale bars: 20 μm FIG. 4 shows:

Stability of antibody-(ED-B) complexes. Analysis of the binding of scFvs E1, H10 and L19 to the ED-B domain of fibronectin. FIG. 4A BIAcore sensograms, showing the improved dissociation profiles obtained upon antibody affinity-maturation. FIG. 4B Native gel electrophoretic analysis of scFv-(ED-B) complexes. Only the high-affinity antibody L19 can form a stable complex with the fluorescently labeled antigen. Fluorescence detection was performed as described (Neri et al. (1996) BioTechniques, 20, 708-712).

FIG. 4C Competition of the scFv-(ED-B-biotin) complex with a 100-fold molar excess of unbiotinylated ED-B, monitored by electrochemiluminescence using an Origen apparatus. A long half-life for the L19-(ED-B) complex can be observed. Black squares: L19; Open triangles: H10.

FIG. 5 shows:

Biodistributions of tumour bearing mice injected with radiolabelled antibody fragments.

Tumour and blood biodistributions, expressed as percent injected dose per gram, are plotted versus time. Relevant organ biodistributions is also reported.

FIG. 6 shows rabbit eyes with implanted polymer pellets soaked with angiogenic substances.

Figure 7:
FIG. 7 shows immunohistochemistry of rabbit cornea sections.

FIG. 7 shows immunohistochemistry of sections of rabbit cornea with new-forming blood vessels, stained with the L19 antibody.

Figure 8:
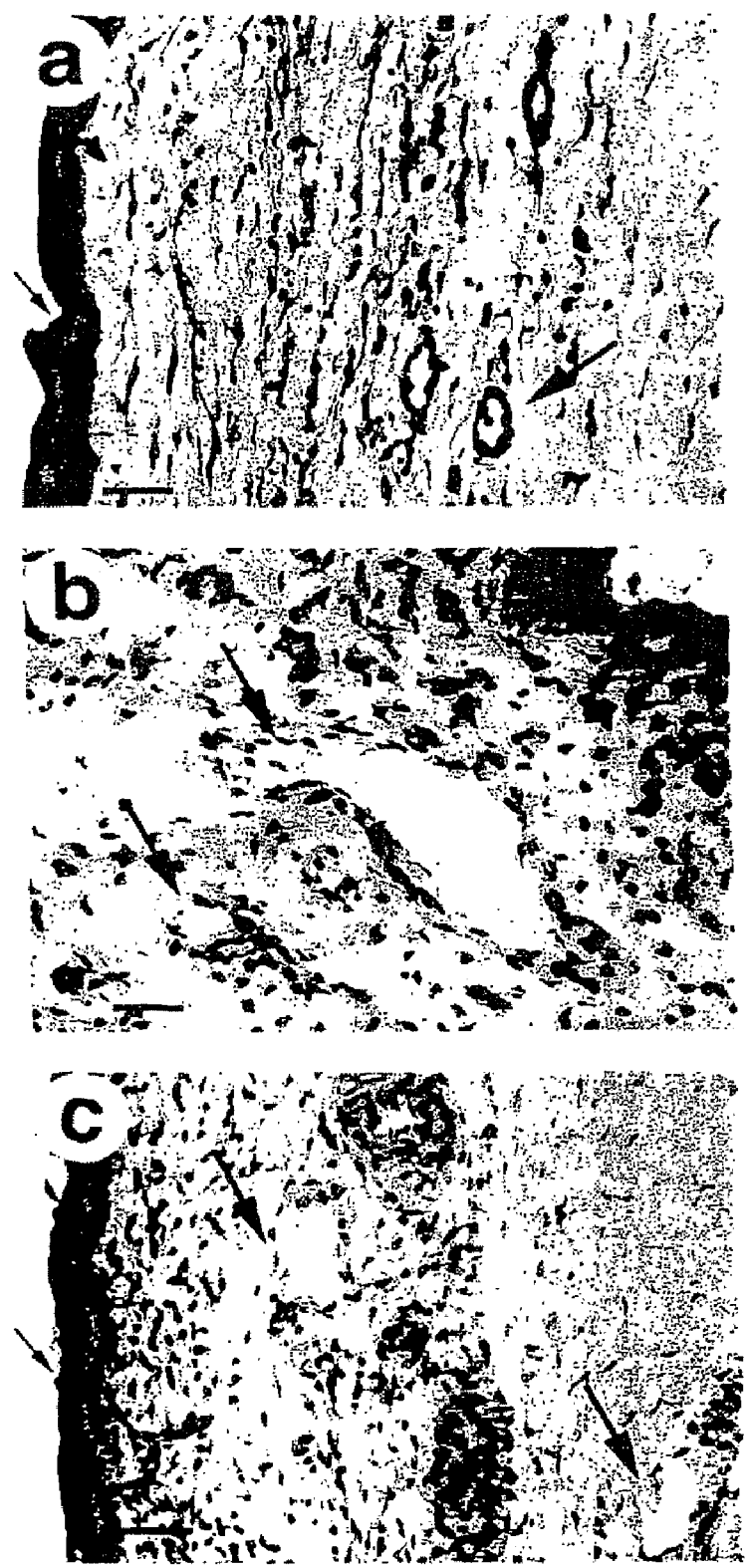
FIG. 8 shows the immunohistochemistry of sections of ocular structures of rabbits (cornea, iris and conjunctiva) using a red alkaline phosphatase substrate and hematoxylin.
Figure 9:
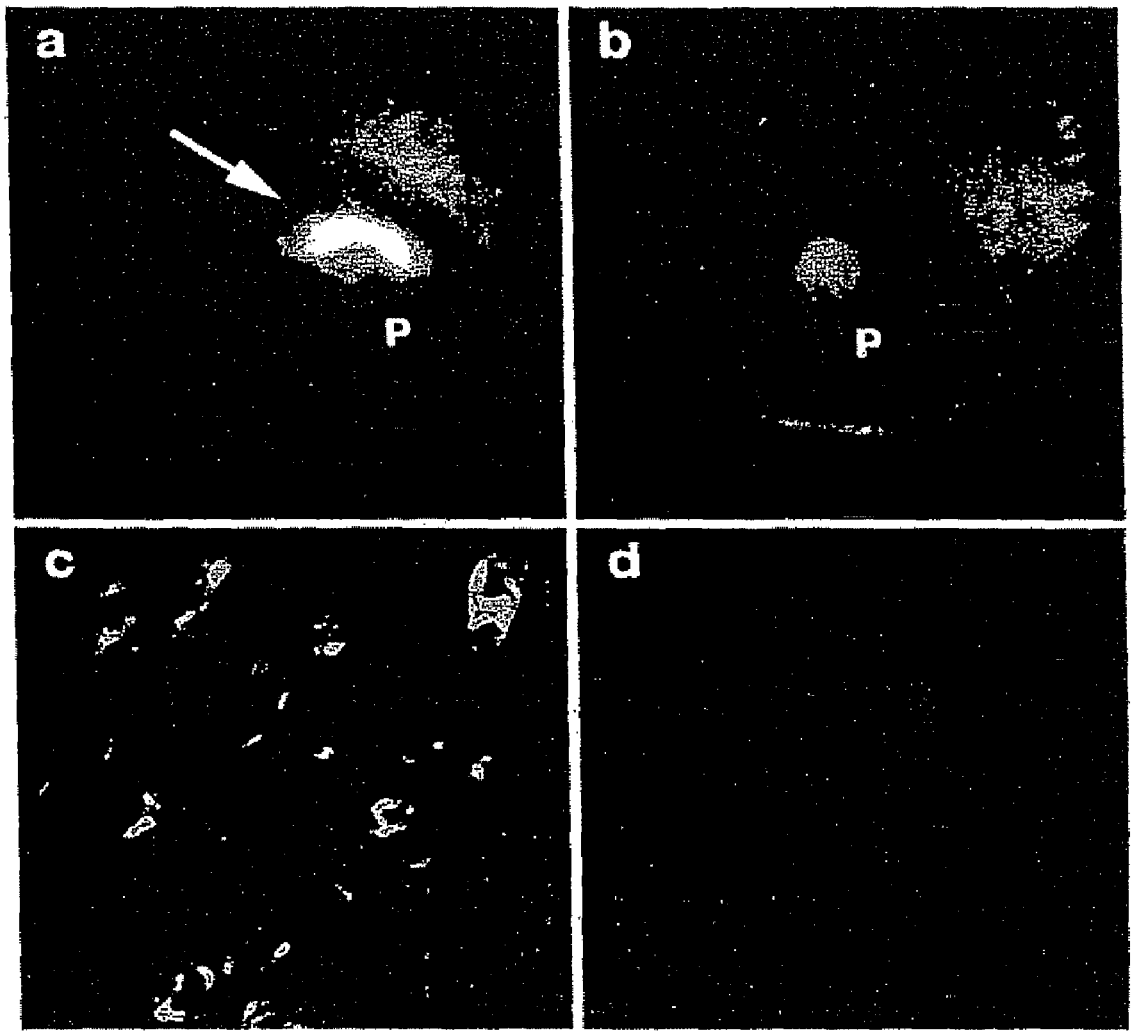
FIG. 9 shows the localisation of fluorescently-labelled antibodies in ocular neovasculature.

FIG. 8 shows immunohistochemical studies of ocular structures using the L19 antibody. A specific red staining is observed around neovascular structures in the cornea (FIG. 8a), but not around blood vessels in the iris (FIG. 8b) and in the conjunctiva (FIG. 8c). Small arrows: corneal epithelium. Relevant blood vessels are indicated with large arrows. Scale bars: 50 μm FIG. 9 shows immunophotodetection of fluorescently labelled antibodies targeting ocular angiogenesis. A strongly fluorescent corneal neovascularisation (indicated by an arrow) is observed in rabbits injected with the antibody conjugate L19-Cy5 (FIG. 9a), specific for the ED-B domain of FN, but not with the antibody HyHEL-10-Cy5 (FIG. 9b). Immunofluorescence microscopy on cornea sections confirmed that L19-Cy5 (FIG. 9c), but not HyHEL-10-Cy5 (FIG. 9d) localises around neovascular structures in the cornea. Images (FIG. 9a,b) were acquired 8 h after antibody injection; (FIG. 9c,d) were obtained using cornea sections isolated from rabbits 24 h after antibody injection. P, pellet.

Figure 10:
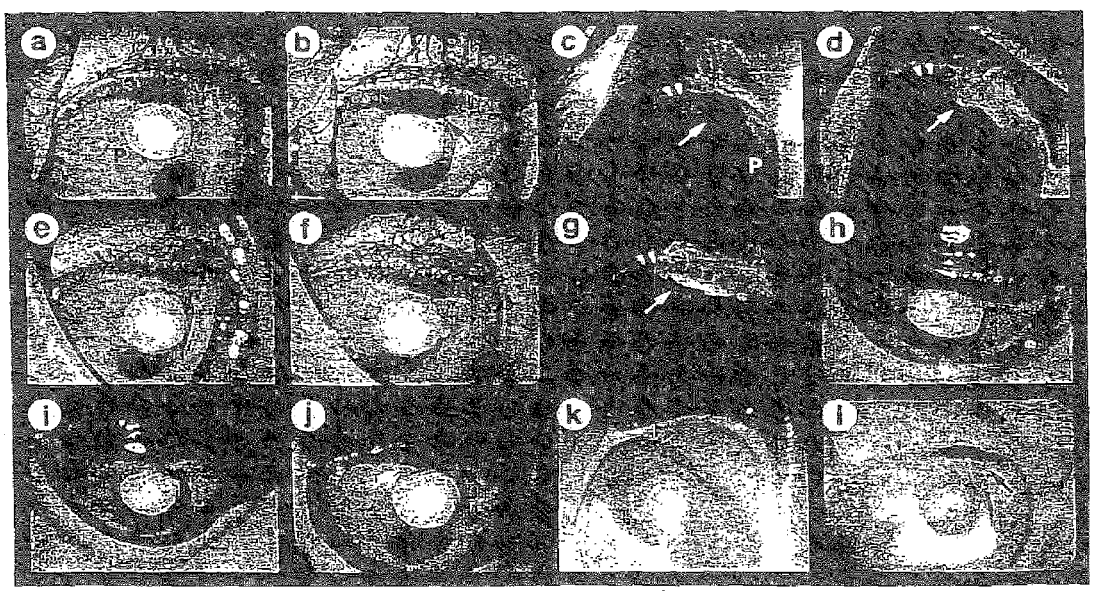
FIG. 10 shows the macroscopic appearance of the eyes of rabbits injected with proteins coupled to photosensitizers, before and after irradiation.

FIG. 10 shows macroscopic images of eyes of rabbits treated with photosensitiser conjugates. Eye of rabbit injected with L19-PS before (FIG. 10a) and 16 h after irradiation with red light (FIG. 10b). The arrow indicates coagulated neovasculature, which is confirmed as a hypofluorescent area in the Cy5 fluoroangiogram of panel (FIG. 10c) 16 h after irradiation. Note that no coagulation is observed in other vascular structures, for example in the dilated conjuctival vessels. For comparison, a Cy5 fluoroangiogram with hyperfluorescence of leaky vessels, and the corresponding colour photograph of untreated rabbit eye are shown in (FIG. 10d) and (FIG. 10h). Pictures (FIGS. 10e, 10f, 10g) are analogous to (FIGS. 10a, 10b, 10c), but correspond to a rabbit injected with ovalbumin-PS and irradiated with red light. No coagulation can be observed, and the angiogram reveals hyperfluorescence of leaky vessels. The eyes of rabbits with early-stage angiogenesis and injected with L19-PS are shown in (FIGS. 10i, 10l). Images before (FIG. 10i) and 16 h after irradiation with red light (FIG. 10j) reveal extensive and selective light-induced intravascular coagulation (arrow). Vessel occlusion (arrow) is particularly evident in the irradiated eye (FIG. 10l) of a rabbit immediately after euthanasia, but cannot be detected in the non-irradiated eye (FIG. 10k) of the same rabbit. P, pellet. Arrowheads indicate the corneo-scleral junction (limbus). In all figures, dilated pre-existing conjunctival vessels are visible above the limbus, whereas growth of corneal neovascularisation can be observed from the limbus towards the pellet (P).

Figure 11:
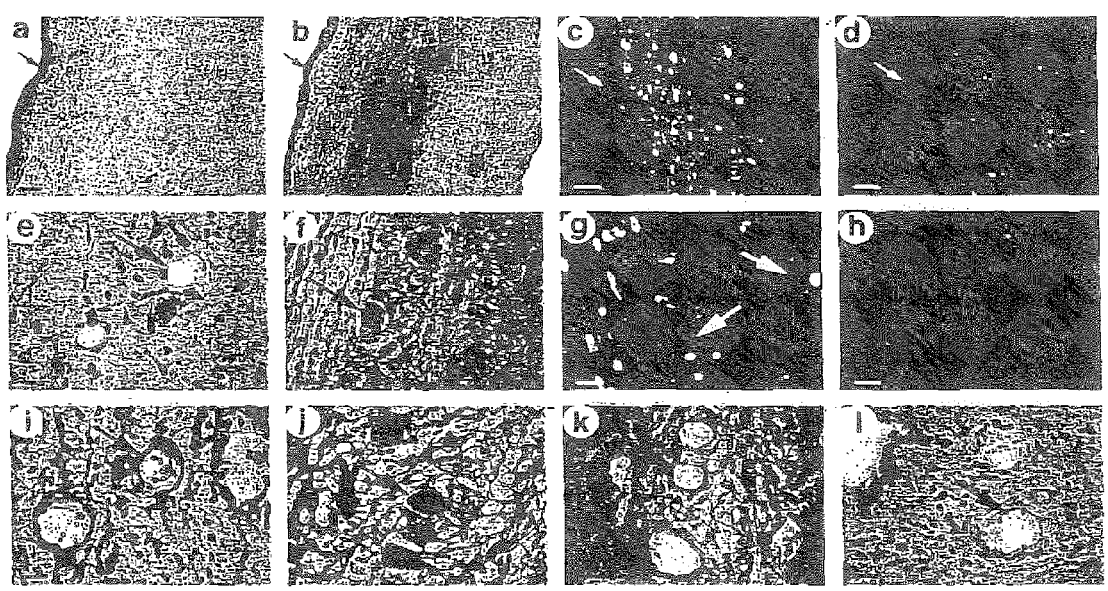
FIG. 11 shows the microscopic analysis of sections of ocular structures of rabbits injected with proteins coupled to photosensitizers and irradiated with red light.

FIG. 11 shows microscopic analysis of selective blood vessel occlusion. H/E sections of corneas (a,e,b,f: non-fixed; i,j: paraformaldehyde fixed) of rabbits injected with ovalbumin-PS (FIGS. 11a, 11e, 11i) or L19-PS (FIGS. 11b, 11f, 11j) and irradiated. Large arrows indicate representative non damaged (FIGS. 11e, 11i) or completely occluded (FIGS. 11f, 11j) blood vessels. In contrast to the selective occlusion of corneal neovasculature and restricted perivascular damage (eosinophilia) mediated by L19-PS after irradiation (FIGS. 11b, 11f, 11j), vessels in the conjunctiva (FIG. 11k) and iris (FIG. 11l) do not show sign of damage in the same rabbit. Fluorescent TUNEL assay indicates the different number of apoptotic cells in sections of irradiated rabbits injected with L19-PS (11c, 11g) or with ovalbumin-PS (11d, 11h). Large arrows indicate some relevant vascular structures. Small arrows indicate corneal epithelium. Scale bars: 100 μm (11a-11d) and 25 μm (11e-11l)

FIG. 12 shows the area under the curve (AUC) of the radioactivity delivered by scFv(L19) to the blood and to the tumour during the first 24 hours after intravenous injection. In this experimental study performed in mice bearing the F9 teratocarcinoma, the AUC of the injected dose of radiolabelled antibody delivered per gram of tumour is 3.6-fold higher than the dose delivered per gram of blood. This ratio increases when the AUC is measured for longer time periods.

Figure 13:
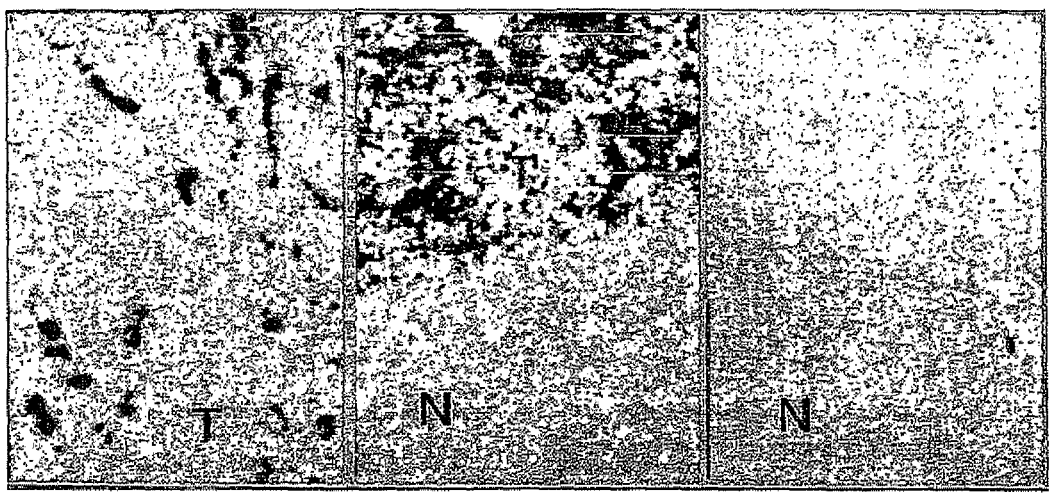
FIG. 13 shows the accumulation of L19 around new vessels.

FIG. 13 shows microautoradiographic analysis of an F9 teratocarcinoma dissected from a nude mouse, after injection of radiolabelled scFv(L19). The pictures show that scFv(L19) accumulates around vascular structure but not in the surrounding normal mouse tissue.

Figure 14:
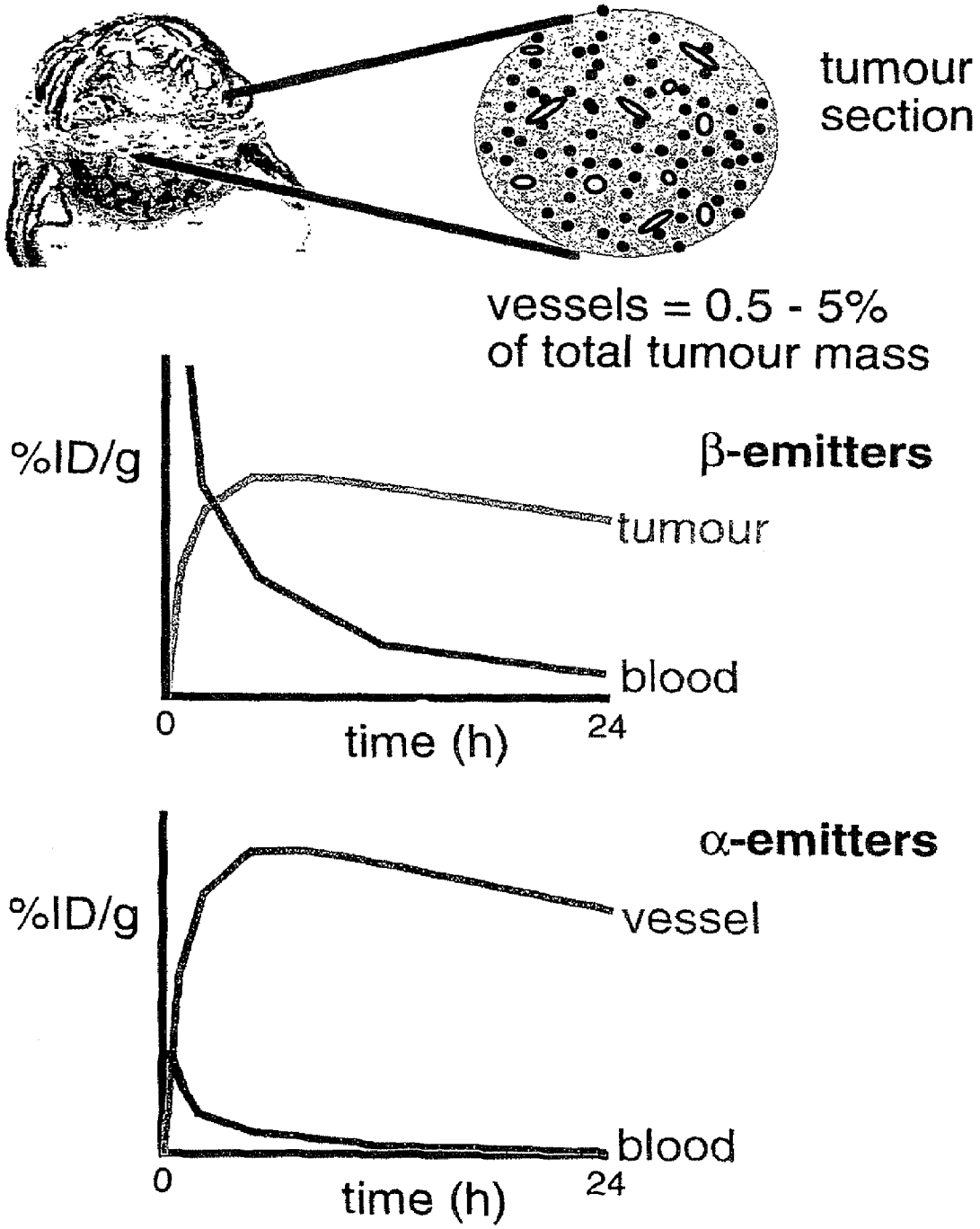
FIG. 14 shows schematic diagrams reporting the relevant % of injected doses per gram, in the case of the L19 antibody coupled to an .alpha.- and .beta.-emitter respectively, plotted versus time.

FIG. 14 illustrates a schematic diagram of the radioimmunotherapy performed with the anti-angiogenesis scFv(L19) coupled with .beta.- or .alpha.-emitting radionuclide. Because new-forming blood vessels in F9 teratocarcinoma constitute 0.5-5% of the total tumour mass, the radioactivity delivered to vascular structures is significantly higher (70-700-fold) than the one delivered to normal tissue and to blood. Coupling scFv(L19) to a beta emitter (e.g., Yttrium-90), the majority of the targeted tumoural area is irradiated, since these .beta.-particles have a range in tissue of several millimeters. On the other hand, coupling scFv(L19) to an alpha emitter (e.g. Astatine-211 or Bismuth-212 or Bismuth-213), the radiation is deposited only around the targeted tumoural blood vessels (penetration: few dozens of micrometers). In this case, the relevant parameters for therapeutic efficacy is the vessel:blood ratio of the percent injected dose of radioactivity per gram of tissue, rather than the tumour:blood ratio (which is the relevant parameter for beta emitting nuclides).

Figure 15:
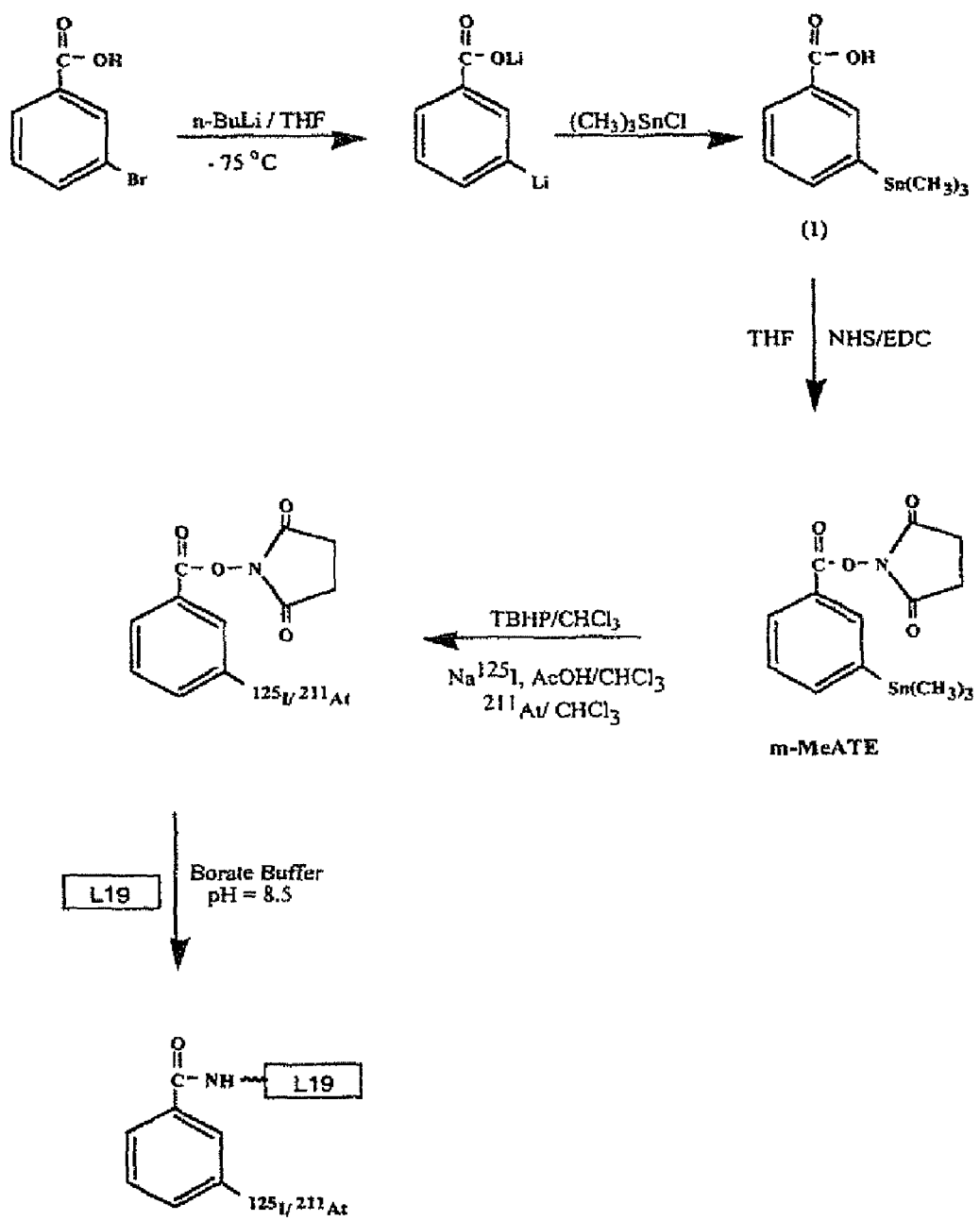
FIG. 15 shows the labelling method according to the Garg protocol modified as described hereinafter.

FIG. 15 shows the procedure for labelling scFv(L19) with Iodine-125 and Astatine-211 using the N-succinimidyl 3-(trimethylstannyl)benzoate (m-MeATE) synthesized from m-bromobenzoic acid.

Figure 16A:
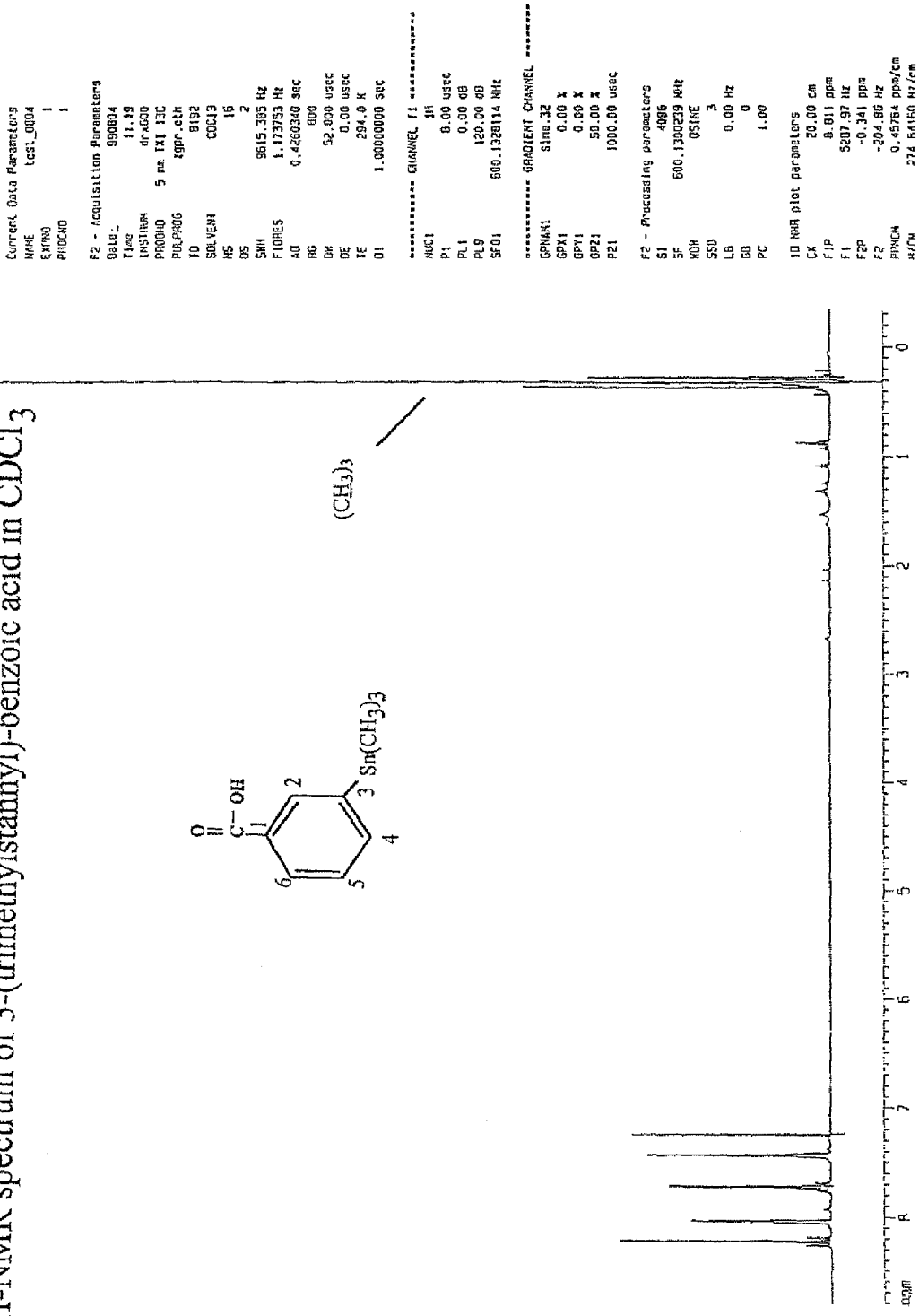

FIG. 16a shows the $^1$H-NMR spectrum of 3-(trimethylstannyl)benzoic acid in $CDCl_3$. The chemical shifts (ppm) are indicated in the X-axis.

FIG. 16b shows the chemical shift in ppm of the protons in the aromatic moiety located at low magnetic field of the NMR spectrum.

Figure 17A:
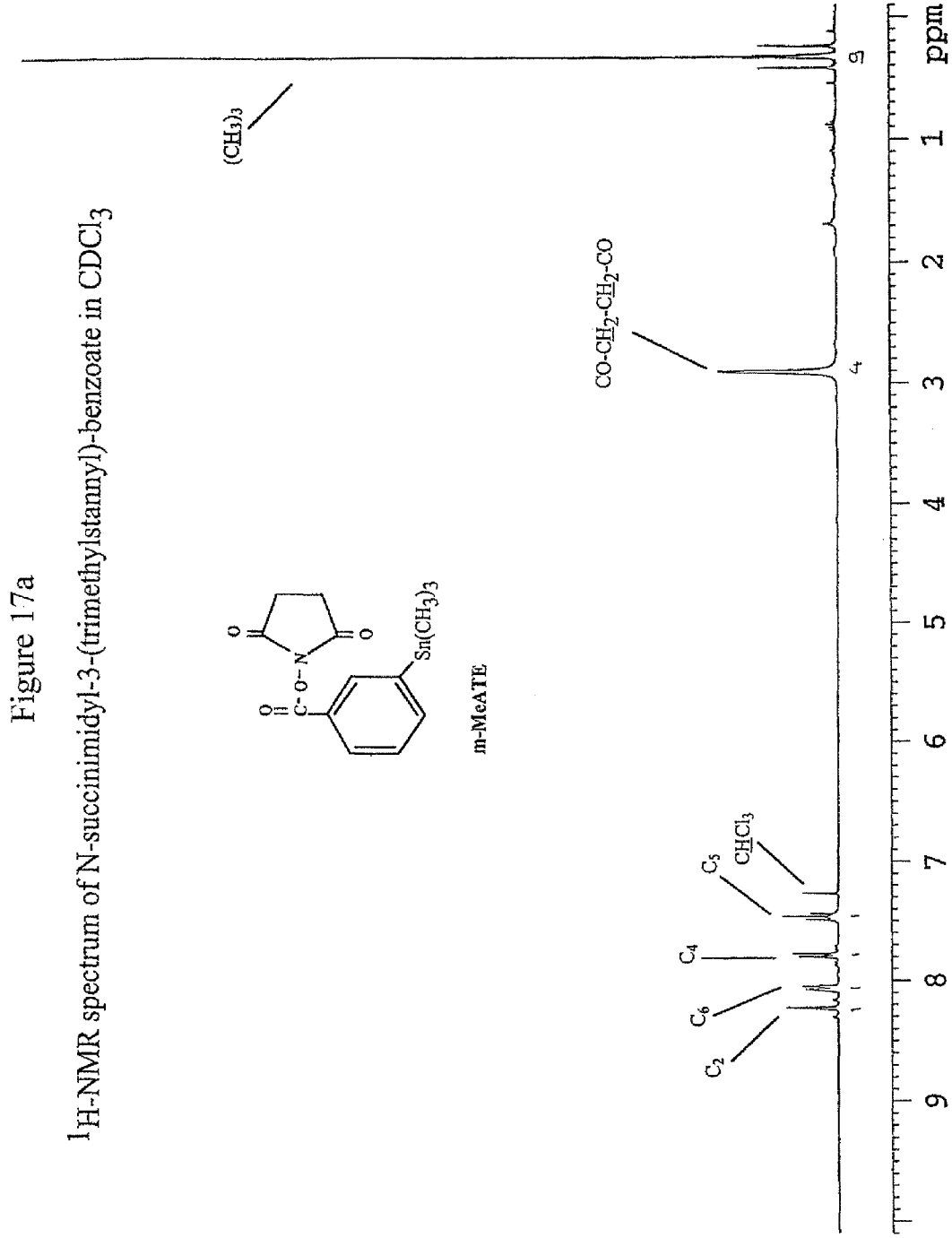
FIGS. 17a and 17b report the 1H-NMR spectrum of N-succinimidyl-3-(trimethylstannyl)-benzoate

FIG. 17a shows the $^1$H-NMR spectrum of m-MeATE in $CDCl_3$. The relative values of peak intensity are reported between the X-axis reporting the chemical shift (ppm) and the spectrum baseline.

Figure 17B:
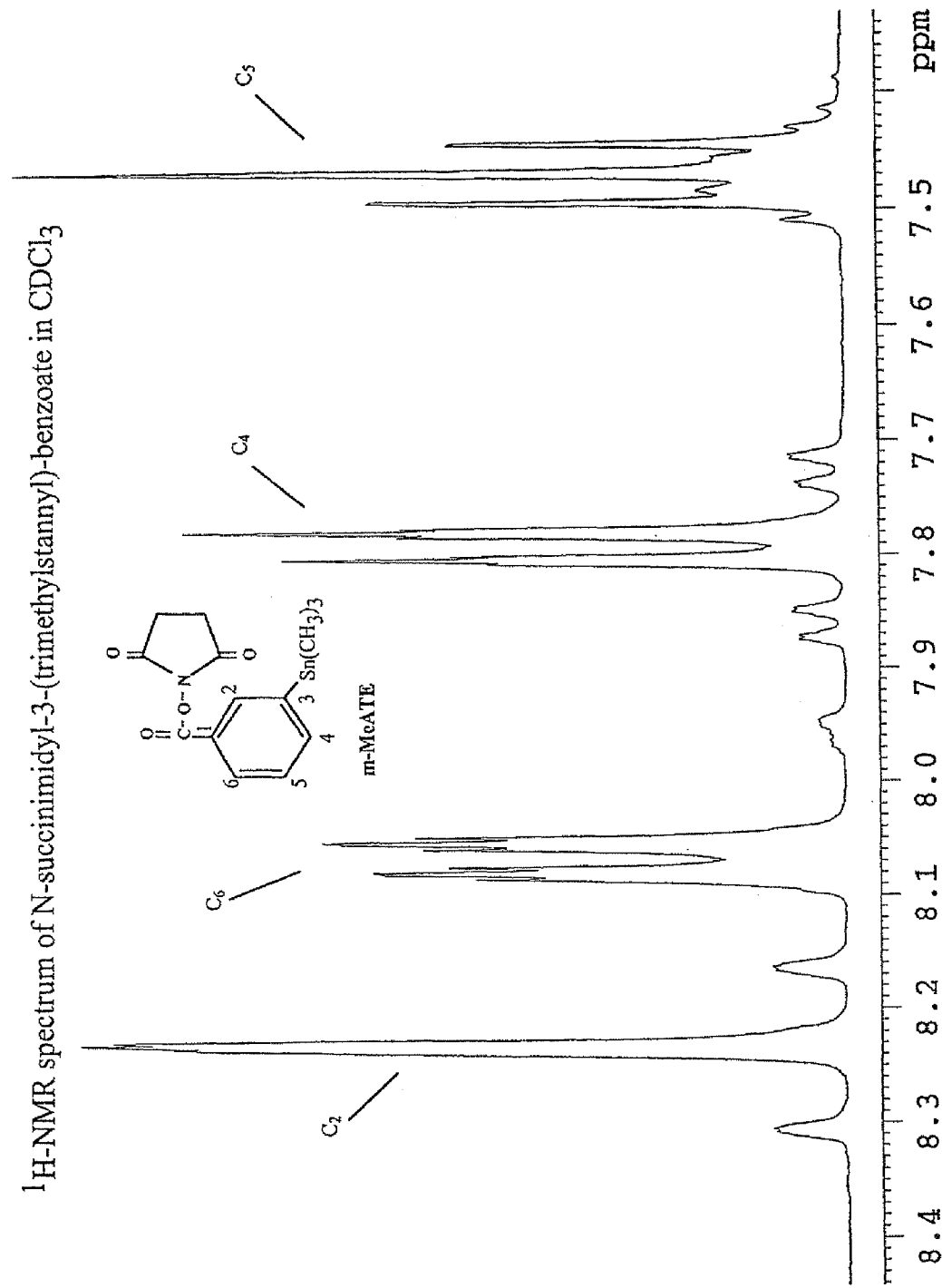

FIG. 17b shows an enlarged portion of the $^1$H-NMR spectrum of m-MeATE.

Figure 18:
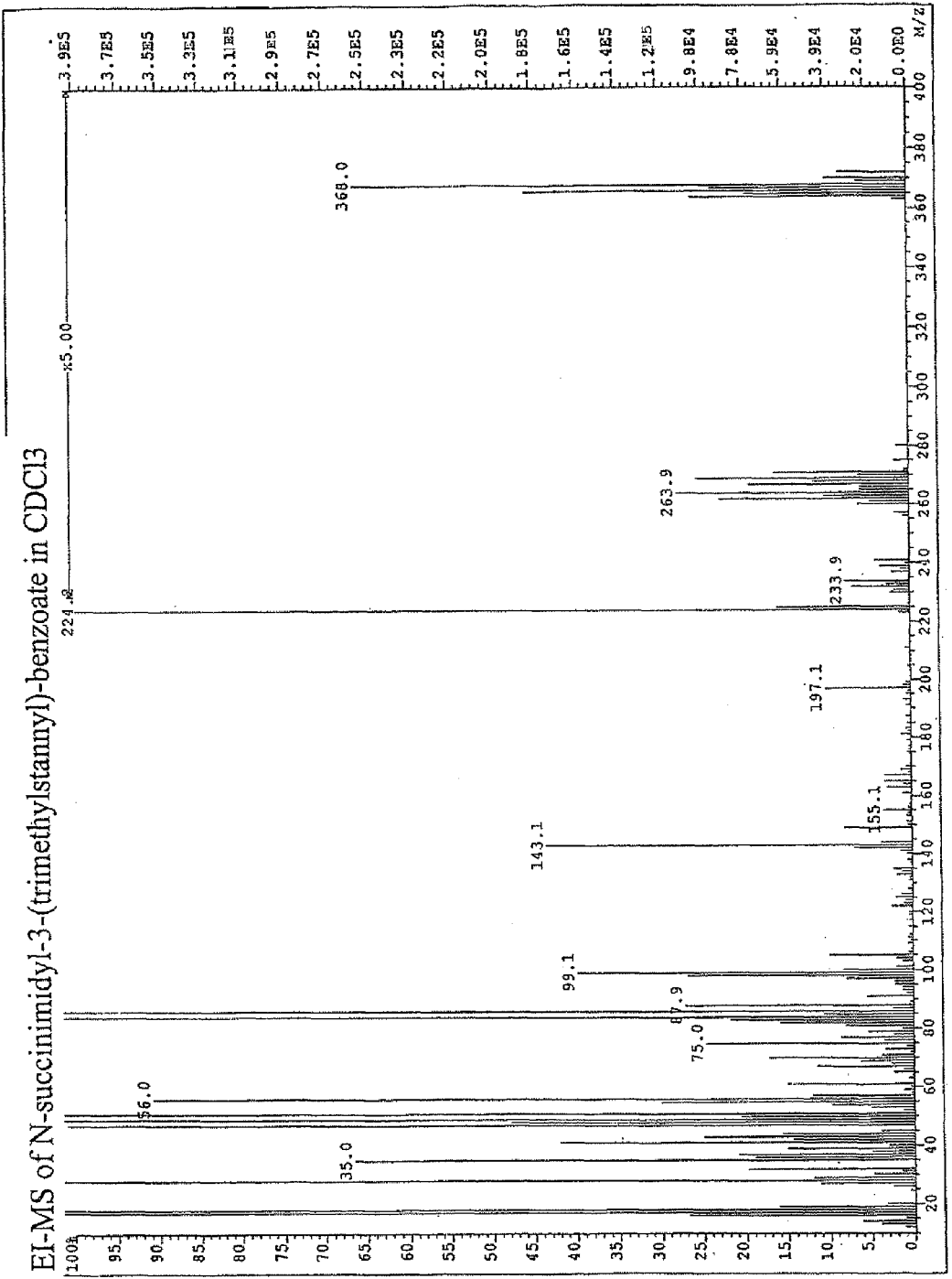
FIG. 18 shows the EI-MS of N-succinimidyl-3-(trimethylstannyl)-benzoate.

FIG. 18 shows the electron ionization mass spectrum (EI-MS) of m-MeATE (molecular weight 383). The mass to charge value (m/e) of 368 represents the mass of the molecular ion $(M^+)$-15 $(CH_3)$.

The invention is more closely described by the following examples.

EXAMPLE 1

Isolation of Human scFv Antibody Fragments Specific for the ED-B Domain of Fibronectin from a Antibody Phage-Display Library A human antibody library was cloned using VH (DP47; Tomlinson et al. (1992). J. Mol. Biol., 227, 776-798.) and Vk (DPK22; Cox et al. (1994). Eur. J. Immunol., 24, 827-836) germline genes (see FIG. 1 for the cloning and amplification strategy). The VH component of the library was created using partially degenerated primers (FIG. 1) in a PCR-based method to introduce random mutations at positions 95-98 in CDR3. The VL component of the library was generated in the same manner, by the introduction of random mutations at positions 91, 93, 94 and 96 of CDR3. PCR reactions were performed as described (Marks et al. (1991). J. Mol. Biol., 222, 581-597). VH-VL scFv fragments were constructed by PCR assembly (FIG. 1; Clackson et al. (1991). Nature, 352, 624-628), from gel-purified VH and VL segments. 30 µg of purified VH-VL scFv fragments were double digested with 300 units each of NcoI and NotI, then ligated into 15 µg of Not1/Nco1 digested pDN332 phagemid vector. pDN332 is a derivative of phagemid pHEN1 (Hoogenboom et al. (1991). Nucl. Acids Res., 19, 4133-4137), in which the sequence between the Not1 site and the amber codon preceding the gene III has been replaced by the following sequence (SEQ ID NO: 25), coding for the D3SD3-FLAG-His6 tag (SEQ ID NO: 26) (Neri et al. (1996). Nature Biotechnology, 14, 385-390):

```
    Not1    D   D   D   S   D   D   D
Y   K   D   D
5'-GCG GCC GCA GAT GAC GAT TCC GAC GAT GAC TAC AAG
GAC GAC

D   D   K   H   H   H   H   H   H   amber
GAC GAC AAG CAC CAT CAC CAT CAC CAT TAG-3'
```

Transformations into TG1 *E. coli* strain were performed according to Marks et al. (1991. J. Mol. Biol., 222, 581-597) and phages were prepared according to standard protocols (Nissim et al. (1991). J. Mol. Biol., 222, 581-597). Five clones were selected at random and sequenced to check for the absence of pervasive contamination.

Recombinant fibronectin fragments ED-B and 7B89, containing one and four type III homology repeats respectively, were expressed from pQE12-based expression vectors (Qiagen, Chatsworth, Calif., USA) as described (Carnemolla et al. (1996). Int. J. Cancer, 68, 397-405).

Selections against recombinant ED-B domain of fibronectin (Carnemolla et al. (1996). Int. J. Cancer, 68, 397-405, Zardi et al. (1987). EMBO J., 6, 2337-2342) were performed at 10 nM concentration using the antigen biotinylated with biotin disulfide N-hydroxysuccinimide ester (reagent B-4531; Sigma, Buchs, Switzerland; 10) and eluted from a 2D gel, and streptavidin-coated Dynabeads capture (Dynal, Oslo, Norway). 1013 phages were used for each round of panning, in 1 ml reaction. Phages were incubated with antigen in 2% milk/PBS (MPBS) for 10 minutes. To this solution, 100 µl Dynabeads (10 mg/ml; Dynal, Oslo, Norway), preblocked in MPBS, were added. After 5 min. mixing, the beads were magnetically separated from solution and washed seven times with PBS-0.1% Tween-20 (PBST) and three times with PBS. Elution was carried out by incubation for 2 min. with 500 µl 50 mM dithiothreitol (DTT), to reduce the disulfide bridge between antigen and biotin. Beads were captured again, and the resulting solution was used to infect exponentially growing TG1 *E. coli* cells. After three rounds of panning, the eluted phage was used to infect exponentially-growing HB2151 *E. coli* cells and plated on (2×TY+1% glucose+100 µg/ml ampicillin)–1.5% agar plates. Single colonies were grown in 2×TY+0.1% glucose+100 µg/ml ampicillin, and induced overnight at 30 degrees with 1 mM IPTG to achieve antibody expression. The resulting supernatants were screened by ELISA using streptavidin-coated microtitre plates treated with 10 nM biotinylated-ED-B, and anti-FLAG M2 antibody (IBI Kodak, New Haven, Conn.) as detecting reagent. 32% of screened clones were positive in this assay and the three of them which gave the strongest ELISA signal (E1, A2 and G4) were sequenced and further characterised.

ELISA assays were performed using biotinylated ED-B recovered from a gel spot, biotinylated ED-B that had not been denatured, ED-B linked to adjacent fibronectin domains (recombinant protein containing the 7B89 domains), and a number of irrelevant antigens. Antibodies E1, A2 and G4 reacted strongly and specifically with all three ED-B containing proteins. This, together with the fact that the three recombinant antibodies could be purified from bacterial supernatants using an ED-B affinity column, strongly suggests that they recognise an epitope present in the native conformation of ED-B. No reaction was detected with fibronectin fragments which did not contain the ED-B domain (data not shown).

In order to test whether the antibodies isolated against a gel spot had a good affinity towards the native antigen, real-time interaction analysis was performed using surface plasmon resonance on a BIAcore instrument as described (Keri et al. (1997) Nature Biotechnol., 15, 1271-1275). Monomeric fractions of E1, A2 and G4 scFv fragments bound to ED-B with affinity in the $10^7$-$10^8 M^{-1}$ range (Table 1).

As a further test of antibody specificity and usefulness, a 2D-PAGE immunoblot was performed, running on gel a lysate of the human melanoma cell line COLO-38, to which minute amounts of the ED-B containing recombinant 7B89 protein had been added (FIG. 2). ScFv(E1) stained strongly and specifically only the 7B89 spot.

Antibodies E1, A2 and G4 were used to immunolocalise ED-B containing fibronectin (B-FN) in cryostat sections of glioblastoma multiforme, an aggressive human brain tumour with prominent angiogenetic processes. FIG. 3 shows serial sections of glioblastoma multiforme, with the typical glomerulus-like vascular structures stained in red by the three antibodies. Immunostaining of sections of glioblastoma multiforme samples frozen in liquid nitrogen immediately after removal by surgical procedures, was performed as described (Carnemolla et al. (1996). Int. J. Cancer, 68, 397-405, Castellani et al. (1994). Int. J. Cancer, 59, 612-618). In short, immunostaining was performed using M2-anti-FLAG antibody (IBI Kodak), biotinylated anti-mouse polyclonal antibodies (Sigma), a streptavidin-biotin alkaline phosphatase complex staining kit (BioSpa, Milan, Italy) and naphtol-AS-MX-phosphate and fast-red TR (Sigma). Gill's hematoxylin was used as a counter-stain, followed by mounting in glycergel (Dako, Carpenteria, Calif.) as previously reported (Castellani et al. (1994). Int. J. Cancer, 59, 612-618).

Using similar techniques and the antibody L19 (see next example) we could also specifically stain new-forming blood vessels induced by implanting in the rabbit cornea polymer pellets soaked with angiogenic substances, such as vascular endothelial growth factor or phorbol esters.

EXAMPLE 2

Isolation of a Human scFv Antibody Fragment Binding to the ED-B with Sub-Nanomolar Affinity ScFv(E1) was selected to test the possibility of improving its affinity with a limited number of mutations of CDR residues located at the periphery of the antigen binding site (FIG. 1A), We combinatorially mutated residues 31-33, 50, 52 and 54 of the antibody VH, and displayed the corresponding repertoire on filamentous phage. These residues are found to frequently contact the antigen in the known 3D-structures of antibody-antigen complexes. The resulting repertoire of $4 \times 10^8$ clones was selected for binding to the ED-B domain of fibronectin. After two rounds of panning, and screening of 96 individual clones, an antibody with 27-fold improved affinity was isolated (H10; Table 1). Similarly to what others have observed with affinity-matured antibodies, the improved affinity was due to slower dissociation from the antigen, rather than by improved kon values (Schier et al. (1996). Gene, 169, 147-155, Ito (1995). J. Mol. Biol., 248, 729-732). The antibody light chain is often thought to contribute less to the antigen binding affinity as supported by the fact that both natural and artificial antibodies devoid of light chain can still bind to the antigen (Ward et al. (1989) Nature, 341, 544-546, Hamers-Casterman et al. (1993). Nature, 363, 446-448). For this reason we chose to randomize only two residues (32 and 50) of the VL domain, which are centrally located in the antigen binding site (FIG. 1a) and often found in 3D structures to contact the antigen. The resulting library, containing 400 clones, was displayed on phage and selected for antigen binding. From analysis of the dissociation profiles using real-time interaction analysis with a BIAcore instrument (Jonsson et al. (1991). BioTechniques, 11, 620-627) and koff measurements by competition experiments with electrochemiluminescent detection a clone (L19) was identified, that bound to the ED-B domain of fibronectin with a Kd=54 pM Table 1.

Affinity maturation experiments were performed as follows. The gene of scFv(E1) was PCR amplified with primers LMB1bis (5'-GCG GCC CAG CCG GCC ATG GCC GAG-3' (SEQ ID NO: 1)) and DP47CDR1for (5'-GA GCC TGG CGG ACC CAG CTC ATM NNM NNM NNGCTA AAG GTG AAT CCA GAG GCT G-3' (SEQ ID NO: 2)) to introduce random mutations at positions 31-33 in the CDR1 of the VH (for numbering: 28), and with primers DP47CDR1back (5'-ATG AGC TGG GTC CGC CAG GCT CC-3' (SEQ ID NO: 3)) and DP47CDR2for (5'-GTC TGC GTA GTA TGT GGT ACC MNN ACT ACC MNN AAT MNN TGA GAC CCA CTC CAG CCC CTT-3' (SEQ ID NO: 4)) to randomly mutate positions 50, 52, 54 in CDR2 of the VH. The remaining fragment of the scFv gene, covering the 3'-portion of the VH gene, the peptide linker and the VL gene, was amplified with primers DP47CDR2back (5'-ACA TAC TAC GCA GAC TCC GTG AAG-3' (SEQ ID NO: 5)) and JforNot (5'-TCA TTC TCG ACT TGC GGC CGC TTT GAT TTC CAC CTT GGT CCC TTG GCC GAA CG-3' (SEQ ID NO: 6)) (94 C 1 min, 60 C 1 min, 72 C 1 min). The three resulting PCR products were gel purified and assembled by PCR (21) with primers LMB1bis and JforNot (94° C. 1 min, 60 C 1 min, 72 C 1 min). The resulting single PCR product was purified from the PCR mix, double digested with NotI/NcoI and ligated into NotI/NcoI digested pDN332 vector. Approximately 9 μg of vector and 3 μg of insert were used in the ligation mix, which was purified by phenolisation and ethanol precipitation, resuspended in 50 μl of sterile water and electroporated in electrocompetent TGI E. coli cells. The resulting affinity maturation library contained $4 \times 10^8$ clones. Antibody-phage particles, produced as described (Nissim et al. (1994). EMBO J., 13, 692-698) were used for a first round of selection on 7B89 coated immunotube (Carnemolla et al. (1996). Int. J. Cancer, 68, 397-405). The selected phages were used for a second round of panning performed with biotinylated ED-B, followed by capture with streptavidin coated magnetic beads (Dynal, Oslo, Norway; see previous paragraph). After selection, approximately 25% of the clones were positive in soluble ELISA (see previous chapter for experimental protocol). From the candidates positive in ELISA, we further identified the one (H10; Table 1) with lowest koff by BIAcore analysis (Jonsson et al. (1991), BioTechniques, 11, 620-627).

The gene of scFv(H10) was PCR amplified with primers LMB1bis and DPKCDR1for (5'-G TTT CTG CTG GTA CCA GGC TAA MNN GCT GCT GCT AAC ACT CTG ACT G (SEQ ID NO: 7)) to introduce a random mutation at position 32 in CDR1 of the VL (for numbering: Chothia and Lesk (1987) J. Mol. Biol., 196, 901-917), and with primers DPKCDR1back (5'-TTA GCC TGG TAC CAG CAG AAA CC-5' (SEQ ID NO: 8)) and DPKCDR2for (5'-GCC AGT GGC CCT GCT GGA TGC MNN ATA GAT GAG GAG CCT GGG AGC C-3' (SEQ ID NO: 9)) to introduce a random mutation at position 50 in CDR2 of the VL. The remaining portion of the scFv gene was amplified with oligos DPKCDR2back (5'-GCA TCC AGC AGG GCC ACT GGC-3' (SEQ ID NO: 10)) and JforNot (94 C 1 min, 60 C 1 min, 72 C 1 min) The three resulting products were assembled, digested and cloned into pDN332 as described above for the mutagenesis of the heavy chain. The resulting library was incubated with biotinylated ED-B in 3% BSA for 30 min., followed by capture on a streptavidin-coated microtitre plate (Boehringer Mannheim GmbH, Germany) for 10 minutes. The phages were eluted with a 20 mM DTT solution (1,4-Dithio-DL-threitol, Fluka) and used to infect exponentially growing TG1 cells.

Analysis of ED-B binding of supernatants from 96 colonies by ELISA and by BIAcore allowed the identification of clone L19. Anti-ED-B E1, G4, A2, H10 and L19 scFv antibody fragments selectively stain new-forming blood vessels in sections of aggressive tumours (FIG. 3).

The above mentioned anti-ED-B antibody fragments were then produced inoculating a single fresh colony in 1 liter of 2×TY medium as previously described in Pini et al. ((1997), J. Immunol. Meth., 206, 171-182) and affinity purified onto a CNBr-activated sepharose column (Pharmacia, Uppsala, Sweden), which had been coupled with 10 mg of ED-B containing 7B89 recombinant protein (Carnemolla et al. (1996). Int. J. Cancer, 68, 397-405). After loading, the column was washed with 50 ml of equilibration buffer (PBS, 1 mM EDTA, 0.5 M NaCl). Antibody fragments were then eluted with triethylamine 100 mM, immediately neutralised with 1 M Hepes, pH 7, and dialysed against PBS. Affinity measurements by BIAcore were performed with purified antibodies as described (Neri et al. (1997). Nature Biotechnol., 15 1271-1275) [FIG. 4]. Band-shift analysis was performed as described (Neri et al. (1996). Nature Biotechnology, 14, 385-390), using recombinant ED-B fluorescently labelled at the N-terminal extremity (Carnemolla et al. (1996). Int. J. Cancer, 68, 397-405, Neri et al. (1997). Nature Biotechnol., 15 1271-1275) with the infrared fluorophore Cy5 (Amersham) [FIG. 4]. BIAcore analysis does not always allow the accurate determination of kinetic parameters for slow dissociation reactions due to possible rebinding effects, baseline instability and long measurement times needed to ascertain that the dissociation phase follows a single exponential profile. We therefore performed measurements of the kinetic dissociation constant koff by competition experiments (Neri et al. (1996), Trends in Biotechnol., 14, 465-470) [FIG. 4]. In brief, anti-ED-B antibodies (30 nM) were incubated with biotinylated ED-B (10 nM) for 10 minutes, in the presence of M2 anti-FLAG antibody (0.5 μg/ml) and polyclonal anti-mouse IgG (Sigma) which had previously been labelled with a ruthenium complex as described (Deaver, D. R. (1995). Nature, 377, 758-760). To this solution, in parallel reactions, unbiotinylated ED-B (1 μM) was added at different times. Streptavidin-coated dynabeads, diluted in Origen Assay Buffer (Deaver, D. R. (1995). Nature, 377, 758-760) were then added (20 μA 1 mg/ml), and the resulting mixtures analysed with a ORIGEN Analyzer (IGEN Inc. Gaithersburg, Md. USA). This instrument detects an electrochemiluminescent signal (ECL) which correlates with the amount of scFv fragment still bound to the biotinylated ED-B at the end of the competition reaction. Plot of the ECL signal versus competition time yields a profile, that can be fitted with a single exponential with characteristic constant koff [FIG. 4; Table 1].

EXAMPLE 3

Targeting Tumours with a High-Affinity Radiolabelled scFv Specific for the ED-B Domain of Fibronectin Radioiodinated scFv(L19) or scFv(D1.3) (an irrelevant antibody specific for hen egg lysozyme) were injected intravenously in mice with subcutaneously implanted murine F9' teratocarcinoma, a rapidly growing aggressive tumour. Antibody biodistributions were obtained at different time points (FIG. 4). ScFv(L19) and scFv(D1.3) were affinity purified on an antigen column (Neri et al. (1997, Nature Biotechnol. 15, 1271-1273) and radiolabelled with iodine-125 using the Iodogen method (Pierce, Rockford, Ill., USA). Radiolabelled antibody fragments retained >80% immunoreactivity, as evaluated by loading the radiolabelled antibody onto an antigen column, followed by radioactive counting of the flow-through and eluate fractions. Nude mice (12 weeks old Swiss nudes, males) with subcutaneously-implanted F9 murine teratocarcinoma (Neri et al. (1997) Nature Biotechnol. 15, 1271-1273) were injected with 3 µg (3-4 µCi) of scFv in 100 µl saline solution. Tumour size was 50-250 mg, since larger tumours tend to have a necrotic centre. However, targeting experiments performed with larger tumours (300-600 mg) gave essentially the same results. Three animals were used for each time point. Mice were killed with humane methods, and organs weighed and radioactively counted. Targeting results of representative organs are expressed as percent of the injected dose of antibody per gram of tissue (% ID/g). ScFv (L19) is rapidly eliminated from blood through the kidneys; unlike conventional antibodies, it does not accumulate in the liver or other organs. Eight percent of the injected dose per gram of tissue localises on the tumour already three hours after injection; the subsequent decrease of this value is due to the fact that the tumour doubles in size in 24-48 hours. Tumour:blood ratios at 3, 5 and 24 hours after injection were 1.9, 3.9 and 11.8 respectively for L19, but always below 1.0 for the negative control antibody.

Radiolabelled scFv(L19) preferentially localises on tumours already few hours after injection, suggesting its usefulness for the immunoscintigraphic detection of angiogenesis in patients.

EXAMPLE 4

Anti-ED-B Antibodies Selectively Stain Newly-Formed Ocular Blood Vessels

Angiogenesis, the formation of new blood vessels from pre-existing ones, is a characteristic process which underlies many diseases, including cancer and the majority of ocular disorders which result in loss of vision. The ability to selectively target and occlude neovasculature will open diagnostic and therapeutic opportunities.

We investigated whether B-FN is a specific marker of ocular angiogenesis and whether antibodies recognising B-FN could selectively target ocular neovascular structures in vivo upon systemic administration. To this aim we stimulated angiogenesis in the rabbit cornea, which allows the direct observation of new-blood vessels, by surgically implanting pellets containing vascular endothelial growth factor or a phorbol ester (FIG. 6). Sucralfate (kind gift of Merck, Darmstadt, Germany)/hydron pellets containing either 800 ng vascular endothelial growth factor (Sigma) or 400 ng phorbol 12-myristate 13-acetate (<<PMA>>; Sigma) were implanted in the cornea of New Zealand White female rabbits as described [D'Amato, R. J., et al., Proc. Natl. Acad. Sci. USA 91, 4082-4085 (1994)]. Angiogenesis was induced by both factors. Rabbits were monitored daily. With both inducers newly formed blood vessels were strongly ED-B-positive in immunohistochemistry. For all further experiments, PMA pellets were used. Immunohistochemical studies showed that L19 strongly stains the neovasculature induced in the rabbit cornea (FIG. 7; 8a), but not pre-existing blood vessels of the eye (FIG. 8b, c) and of other tissues (data not shown). Immunohistochemistry was performed as described [Carnemolla, B. et al., Int. J. Cancer 68, 397-405 (1996)].

EXAMPLE 5

The Human Antibody Fragment L19, Binding to the ED-B with Sub-Nanomolar Affinity, Targets Ocular Angiogenesis In Vivo Using the rabbit cornea model of angiogenesis described in the previous example, and an immunophotodetection methodology [Neri, D. et al., Nature Biotechnol. 15, 1271-1275 (1997)], we demonstrated that L19, chemically coupled to the red fluorophore Cy5, but not the antibody fragment (HyHEL-10)-Cy5 directed against an irrelevant antigen (FIG. 9a,b), selectively targets ocular angiogenesis upon intravenous injection. Fluorescent staining of growing ocular vessels was clearly detectable with L19 immediately after injection, and persisted for at least two days analogous to previous observations with tumour angiogenesis. Subsequent ex vivo immunofluorescent microscopic analysis on cornea sections confirmed the localisation of L19, but not of HyHEL-10, around vascular structures (FIG. 9c,d). The demonstration of the antibody-based selective targeting of ocular neovascularisation, together with the reactivity of anti-B-FN antibodies in different species, warrants future clinical investigations. Immunofluorescence imaging could be useful for the early detection of ocular angiogenesis in risk patients, before lesions become manifest in fluoroangiography.

Some methodological details:

For ex vivo immunofluorescence and for some H/E stainings, corneas were fixed in 4% paraformaldehyde in PBS before embedding. Fluorescence photodetection experiments were performed with rabbits sedated using 5 mg/kg Acepromazin. For targeting experiments, 3.5 mg of scFv(L19)$_1$-Cy5$_{0.66}$ and 2.8 mg of scFv(HyHEL-10)$_1$-Cy5$_{0.83}$ were injected intravenously in each rabbit (injection time=15 min). A strong fluorescence in the corneal neovasculature was observed already immediately after injection of L19, but not of HyHEL-10, and persisted for several hours. As an additional test of specificity, rabbits injected the previous day with scFv(HyHEL-10)-Cy5 and negative in the fluorescence photodetection, were injected the next day with scFv(L19)-Cy5, and showed a strong fluorescent staining of corneal angiogenesis.

For fluorescence detection, the eye was illuminated with a tungsten halogen lamp (model Schott KL1500; Zeiss, Jena, Germany) equipped with a Cy5-excitation filter (Chroma, Brattleboro, Vt., U.S.A.) and with two light guides whose extremities were placed at approximately 2 cm distance from the eye. Fluorescence was detected with a cooled C-5985 monochrome CCD-camera (Hamamatsu, Hamamatsu-City, Japan), equipped with C-mount Canon Zoom Lens (V6×16; 16-100 mm; 1:1.9) and a 50 mm diameter Cy5 emission filter (Chroma), placed at 3-4 cm distance from the irradiated eye. Acquisition times were 0.4 s.

Cy5 fluoroangiography experiments were performed with the same experimental set up, but injecting intravenously 0.25 mg Cy5-Tris (the reaction product between Cy5-NHS and tris[hydroxymethyl]aminomethane; injection time=5 s). Acquisition times were 0.2 s.

Antibody fragments were in scFv format. The purification of scFv(L19) and scFv(HyHEL-10) and their labeling with the N-hydroxysuccinimide (NHS) esters of indocyanine dyes have been described elsewhere [Neri, D. et al., *Nature Biotechnol.* 15, 1271-1275 (1997); Fattorusso, R., et al. (1999) *Structure,* 7, 381-390]. Antibody: Cy5 labeling ratios for the two antibodies were 1.5:1 and 1.2:1, respectively. Cy5-NHS was purchased from Amersham Pharmacia Biotech (Zurich, Switzerland), ovalbumin from Sigma (Buchs, Switzerland).

After the labeling reaction, antibody conjugates were separated from unincorporated fluorophore or photosensitiser using PD-10 columns (Amersham Pharmacia Biotech) equilibrated in 50 mM phosphate, pH 7.4, 100 mM NaCl (PBS). Immunoreactivity of antibody conjugates was measured by affinity chromatography on antigen columns [Neri, D. et al., *Nature Biotechnol.* 15, 1271-1275 (1997)] and was in all cases >78%. Immunoconjugates were analysed by sodium dodecyl sulfate polyacrylamide gel electrophoresis and migrated as a band of MW=30'000 Dalton (purity=90%).

EXAMPLE 6

The Human Antibody Fragment L19, Chemically Conjugated to the Photosensitiser Sn (IV) Chlorine e6, Selectively Targets Ocular Angiogenesis and Mediates its Occlusion upon Irradiation with Red Light To test whether selective vessel ablation could be achieved by virtue of the antibody-mediated targeting, we injected rabbits with the L19 antibody fragment or an irrelevant protein that does not localise in newly formed blood vessels (ovalbumin) coupled to the photosensitiser tin (IV) chlorin $e_6$ (hereafter named <<PS>>). The eyes of injected animals were irradiated with red light (light dose=78 J/cm$^2$). Representative results are depicted in FIG. 10. A striking macroscopic difference was observed 16 h after irradiation in rabbits treated with L19-PS (FIG. 10a,b), with coagulation of the corneal neovasculature but not of vessels in the conjunctiva or in other ocular structures. Fluoroangiography with the indocyanine fluorophore Cy5 (FIG. 10c) confirmed vessel occlusion as a characteristic hypofluorescent area. On the contrary, hyperfluorescent areas were observed in the leaky neovasculature of non-irradiated eyes (FIG. 10d,h). No macroscopic alteration was detectable in the irradiated vessels of rabbits treated with ovalbumin-PS (FIG. 10e-g), either ophthalmoscopically or by Cy5 fluoroangiography. The effect of irradiation of the targeted L19-PS conjugate at early stages of corneal angiogenesis are shown in FIG. 10i-l. Selectively coagulated blood vessels were macroscopically visible in live animals (FIG. 10i,j) and even more evident in animals immediately after euthanasia (FIG. 10k,l). Photodynamic damage was further investigated using microscopic techniques. After irradiation, vessel occlusion could be detected by standard hematoxylin/eosin (H/E) staining techniques in both non-fixed and paraformaldehyde-fixed cornea sections of animals treated with L19-PS (FIG. 10b,f,j), but not of those treated with ovalbumin-PS (FIG. 10a,e,i). Apoptosis in the portion of the cornea targeted by the photosensitiser conjugate was clearly visible in the fluorescent TUNEL assay (FIG. 10c,g), but hardly detectable ink negative controls (FIG. 10d,h). A higher magnification view showed apoptosis of endothelial cells in vascular structures (FIG. 10g). No damage to blood vessels of the iris, sclera and conjunctiva of treated animals could be observed either by TUNEL assay (not shown) or by H/E staining (FIG. 10k,l).

Selective photodynamic ablation of neovasculature promises to be beneficial for the treatment of ocular disorders and of other angiogenesis-related pathologies that are accessible to irradiation using light diffusers or fibre optic techniques. The results of this study clearly demonstrate that ocular neovasculature can be selectively occluded without damaging pre-existing blood vessels and normal tissues.

Some methodological details:

Tin (IV) chlorin $e_6$ was selected from a panel of photosensitisers, on the basis of their potency, solubility and specificity, after coupling to a rabbit anti-mouse polyclonal antibody (Sigma). These immunoconjugates were screened by targeted photolysis of red blood cells coated with a monoclonal antibody specific for human CD47 (#313441A; Pharmingen, San Diego Calif., U.S.A.). Tin (IV) chlorin $e_6$ was prepared as described [Lu, X. M. et al., *J. Immunol. Methods* 156, 85-99 (1992)]. For coupling to proteins, tin (IV) chlorin $e_6$ (2 mg/ml) was mixed for 30 min at room temperature in dimethylformamide with a ten-fold molar excess of EDC (N'-3-dimethylaminopropyl-N-ethylcarbodiimide hydrochloride, Sigma) and NHS(N-hydoxysuccinimide, Sigma). The resulting activated mixture was then added to an eight-fold larger volume of protein solution (1 mg/ml) and incubated at room temperature for 1 h.

After the labeling reaction, antibody conjugates were separated from unincorporated fluorophore or photosensitiser using PD-10 columns (Amersham Pharmacia Biotech) equilibrated in 50 mM phosphate, pH 7.4, 100 mM NaCl (PBS). Immunoreactivity of antibody conjugates was measured as described in the previous Example.

For photokilling experiments, rabbits were injected intravenously with 12 mg scFv(L19)$_1$-tin (IV) chlorin e6$_{0.8}$ or 38 mg ovalbumin$_1$-tin (IV) chlorin e6$_{0.36}$, and kept in the dark for the duration of the experiment. Eight hours after injection, rabbits were anesthesised with ketamin (35 mg/kg)/xylazine (5 mg/kg)/acepromazin (1 mg/kg), and one of the two eyes was irradiated for 13 min with a Schott KL1500 tungsten halogen lamp equipped with a Cy5 filter (Chroma) and with two light guides whose extremities were placed at 1 cm distance from the eye. The illuminated area was approximately 1 cm$^2$, with an irradiation power density of 100 mW/cm$^2$, measured using a SL818 photodetector (Newport Corp., Irvine, Calif., U.S.A.). No sign of animal discomfort after irradiation was observed. As a preventive measure, rabbits received analgesics after irradiation (buprenorphine 0.03 mg/Kg). To monitor photokilling, eyes were investigated with an ophthalmoscope and photographed using a fundus camera KOWA SL-14 (GMP SA, Rennens, Lausanne, Switzerland). Five rabbits were treated with each of the tin (IV) chlorin $e_6$ conjugates and irradiated in one eye only, the other eye serving as an internal negative control. As additional control, two rabbits were irradiated only, but received no photosensitiser conjugate.

Immediately after rabbits' euthanasia with an overdose of anaesthetic, eyes were enucleated, corneas removed, then embedded in Tissue Tek (Sakura Finetechnical, Tokyo, Japan) and frozen. For ex vivo immunofluorescence and for some H/E stainings, corneas were fixed in 4% paraformaldehyde in PBS before embedding. Cryostat sections of 5 μm were used for further microscopic analysis. Fluorescent TUNEL assays were performed according to manufacturer's instructions (Roche Diagnostic, Rotkreuz, Switzerland).

EXAMPLE 7

Conjugation of Astatine-211 to Human Antibody Fragment L19 Through m-MeATE A solution of m-bromobenzoic acid (1 g, 5 mmol) in 25 ml of dry tetrahydrofuran (THF) is placed in a 250 ml, two-necked round bottom flask, maintained under nitrogen atmosphere and cooled to −75° C. using (ether:dry ice) bath. To the above, 6.25 ml of n-buthyl lithium (1.6M solution in hexane) is added slowly over 25 min. The dilithio anion thus generated is stirred for an additional 10 min. Still under a nitrogen atmosphere, trimethylstannyl chloride (1.09 mg, 5.47 mmol) dissolved in 10 ml dry THF is added over 20 min to the reaction mixture. The cooling bath is removed and the reaction is slowly brought to room temperature (RT) and stifling is kept for 1 hour. The reaction is quenched by addition of water (10 ml) and extracted three times with 100 ml of diethyl ether. The organic phase is washed with 5% $NaHCO_3$ (2×25 ml) and water (2×20 ml). After drying over $MgSO_4$, it is concentrated on a rotary evaporator. Thin layer chromatography (TLC) is performed on analytical, pre-coated silica gel plastic plates using the following mobile phase: Hexane:ethylacetate(EtOAc):acetic acid (AcOH) (70:29.7:0.3). 3-(trimethylstannyl) benzoate (Rf=0.46) is purified by gravimetric chromatography using a silica gel 60 column (40-63μ, 4 200×3 mm) eluted with the same phase above reported. We obtain 100 mg (0.35 mmol) of product, in 7% yield as an oil. The assigned structure ($^1$H-NMR) is reported in FIG. 16a,b.

To the stannyl ester resuspended in THF (10 ml), N-hydroxy-succinimide (48.34 mg, 0.42 mmol) and diciclohexylcarbodiimide (86.66 mg, 0.42 mmol) are added and stirred overnight at room temperature. Precipitated dicyclohexylurea is filtered off and the solvent is evaporated on a rotary evaporator to give an oil. The desired m-MeATE (Rf=0.34) is isolated by gravimetric chromatography with Hexane:EtOAc (2:1) using a silica gel 60 column. After evaporation of the solvent we obtain 92.3 mg (0.241 mmol) of m-MeATE in 68.8% relative yield. The assigned structure is confirmed by $^1$H-NMR and Mass Spectroscopy (FIGS. 17a,b and 18). This bifunctional compound is used to couple scFv(L19) to the alpha-emitting radionuclide Astatine-211.

In a glove-box previously inflated with inert gas, 1.9 mg of m-MeATE (5 μmol) and tert-butyl hydroperoxide (20 μmol) are added to the chloroform trap containing 1 mCi $^{211}$At anion. The reaction is kept at room temperature for 15 minutes and the mixture is purified using a disposable Sep-Pak silica gel cartridge. The reaction mixture is added to 300 μl of Hexane and loaded on the column previously equilibrated with Hexane. Following washing with Hexane (40 ml) and 8% ethylacetate in Hexane (25 ml), the product N-succinimidyl 3-$^{211}$At-benzoate is isolated in 30% ethylacetate in Hexane (ca. 15 ml). The radionuclide incorporation in the bifunctional agent m-MeATE is measured using an automated gamma counter with an energy window set to include the Polonium K X-rays emitted in the decay of $^{211}$At. The eluted fraction is evaporated and resuspended in dimethyl sulfoxide (100 μl) and then added to 200 μl of borate buffer (pH=8.5) containing 13 nmoles of scFv (L19). The reaction is stirred at room temperature for 30 minutes and the L19-$^{211}$At conjugate is purified using a PD-10 disposable gel filtration column. Antibody immunoreactivity after labeling is evaluated by loading an aliquot of radiolabeled sample onto 200 μl of ED-B-Sepharose resin (capacity, >2.5 mg ED-B/ml resin) on a pasteur pipette, followed by radioactive counting of the flow-through and eluate fractions. Immunoreactivity, defined as the ratio between the counts of the eluted protein and the sum of the counts of the eluted and flow-through fractions, is >80%.

TABLE 1

Sequences of selected anti-ED-B antibody clones. The column labeled "50-54*" discloses SEQ ID NOS 27, 27, 27, 28 and 28, respectively, in order of appearance. The column labeled "95-98" discloses SEQ ID NOS 29, 30, 31, 31 and 31, respectively, in order of appearance. The column labled "91-96*" discloses SEQ ID NOS 32, 33, 34, 34 and 34, respectively, in order of appearance.

| Clone | VH chain | | | | VL chain | |
|---|---|---|---|---|---|---|
|  | 31-33* | 50-54* | 95-98* | 32* | 50* | 91-96* |
| A2 | SYA | AISGSG | GLSI | Y | G | NGWYPW |
| G4 | SYA | AISGSG | SFSF | Y | G | GGWLPY |
| E1 | SYA | AISGSG | FPFY | Y | G | TGRIPP |
| H10 | SFS | SIRGSS | FPFY | Y | G | TGRIPP |
| L19 | SFS | SIRGSS | FPFY | Y | Y | TGRIPP |

Relevant amino acid positions (*: numbering according to Tomlinson et al. (1995) EMBO J., 14, 4628-4638) of antibody clones isolated from the designed synthetic libraries. Single amino acid codes are used according to standard IUPAC nomenclature.

TABLE 2

Affinities of anti-ED-B scFv fragments

| Clone | kon ($s^{-1}M^{-1}$) | koff ($s^{-1}$)$^B$ | koff ($s^{-1}$)$^C$ | $K_d$ (M)* |
|---|---|---|---|---|
| A2 | $1.5 \times 10^5$ | $2.8 \times 10^{-3}$ | — | $1.9 \times 10^{-8}$ |
| G4 | $4.0 \times 10^4$ | $3.5 \times 10^{-3}$ | — | $8.7 \times 10^{-8}$ |
| E1 | $1.6 \times 10^5$ | $6.5 \times 10^{-3}$ | — | $4.1 \times 10^{-8}$ |
| H10 | $6.7 \times 10^4$ | $5.6 \times 10^{-4}$ | $9.9 \times 10^{-5}$ | $1.5 \times 10^{-9}$ |
| L19 | $1.1 \times 10^5$ | $9.6 \times 10^{-5}$ | $6.0 \times 10^{-6}$ | $5.4 \times 10^{-11}$ |

*$K_d = k_{off}/k_{on}$. For the high-affinity binders H10 and L19, $k_{off}$ values from BIAcore experiments are not sufficietly reliable due to effects of the negatively-charged carboxylated solid dextran matrix; Kd values are therefore calculated from $k_{off}$ measurements obtained by competition experiments (Experimental Procedures).$k_{off}$, kinetic dissociation constant; $k_{on}$, kinetic assocation constant; $K_d$, dissociation constant. B = measured on the BIAcore; C = measured by competition with electrochemiluminescent detection. Values are accurate to +/−50%, on the basis of the precision of concentration determinations.

The invention claimed is:

1. A conjugate comprising (a) an scFv antibody with specific, high affinity for the ED-B domain of fibronectin which has the amino acid sequence encoded by the DNA insert of ATCC deposit no. PTA-9529 and (b) a molecule capable of inducing blood coagulation and blood vessel occlusion.

2. A conjugate according to claim 1 wherein the molecule capable of inducing blood coagulation and blood vessel occlusion is a photoactive molecule.

3. A conjugate according to claim 1 wherein the photoactive molecule is a photosensitizer.

4. A conjugate according to claim 3 wherein the photosensitizer absorbs at a wavelength above 600 nm.

5. A conjugate according to claim 3 wherein the photosensitizer is a derivative of tin (IV) chlorin e6.

6. A method for the treatment of an angiogenesis-related pathology in a patient comprising administering a conjugate according to claim 3 by injections, followed by irradiating said patient.

7. A method according to claim 6 wherein the angiogenesis-related pathology treated is caused by or associated with ocular angiogenesis.

8. A conjugate according to claim 1 wherein the molecule capable of inducing blood coagulation and blood vessel occlusion is a radionuclide.

9. A conjugate according to claim 8 wherein the radionuclide is a β-emitting radionuclide.

10. A method for the treatment of an angiogenesis-related pathology comprising administering a radionuclide-containing conjugate according to claim 8 by injection.

11. A method according to claim 10 wherein the radionuclide is astatine-211.

12. A method for the treatment of an angiogenesis-related pathology in a patient comprising administering a conjugate according to claim 1.

13. A conjugate of claim 1 wherein the antibody is radiolabeled.

14. A conjugate of claim 13 wherein the antibody is radioiodinated.

15. A diagnostic kit comprising a conjugate of claim 13 and one or more reagents for detecting angiogenesis.

16. A conjugate of claim 1 wherein the antibody is produced recombinantly.

17. An scFv antibody with specific, high affinity for the ED-B domain of fibronectin which has the amino acid sequence encoded by the DNA insert of ATCC deposit no. PTA-9529.

* * * * *

UNITED STATES PATENT AND TRADEMARK OFFICE
CERTIFICATE OF CORRECTION

PATENT NO. : 8,097,254 B2
APPLICATION NO. : 10/821930
DATED : January 17, 2012
INVENTOR(S) : Neri et al.

It is certified that error appears in the above-identified patent and that said Letters Patent is hereby corrected as shown below:

On the Title Page, Item (75), "Genoa (IT); Manfred Birchler, Zürich" should read
-- Genova (IT); Manfred Birchler, Zürich --.

In the Claims

Column 35, line 62, Claim 3 reads "3. A conjugate according to claim 1 wherein the photoac-" should read -- 3. A conjugate according to claim 2 wherein the photoac- --.

Signed and Sealed this
Eleventh Day of June, 2013

Teresa Stanek Rea
*Acting Director of the United States Patent and Trademark Office*